United States Patent
Jon et al.

(10) Patent No.: US 10,131,693 B2
(45) Date of Patent: Nov. 20, 2018

(54) BIPODAL-PEPTIDE BINDER

(75) Inventors: Sang Yong Jon, Gwangju (KR); Sung Hyun Kim, Gwangju (KR); Se Ho Park, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 12/999,717

(22) PCT Filed: Oct. 20, 2009

(86) PCT No.: PCT/KR2009/006059
§ 371 (c)(1),
(2), (4) Date: Feb. 23, 2011

(87) PCT Pub. No.: WO2010/047515
PCT Pub. Date: Apr. 29, 2010

(65) Prior Publication Data
US 2011/0152500 A1    Jun. 23, 2011

(30) Foreign Application Priority Data

Oct. 20, 2008 (KR) .................. 10-2008-0102648

(51) Int. Cl.
*C07K 14/00* (2006.01)
*A61K 49/00* (2006.01)

(52) U.S. Cl.
CPC ........ *C07K 14/001* (2013.01); *A61K 49/0032* (2013.01); *A61K 49/0056* (2013.01)

(58) Field of Classification Search
CPC ............... C12Q 1/6886; C12Q 1/6883; C12Q 2600/136; C12Q 1/6837; C12N 15/115;
(Continued)

(56) References Cited

U.S. PATENT DOCUMENTS 5,427,908 A    6/1995  Dower et al.
5,720,937 A *  2/1998  Hudziak et al. ............. 424/9.34
(Continued)

FOREIGN PATENT DOCUMENTS

WO    WO 00/60070 A1    10/2000

OTHER PUBLICATIONS

Scherf et al. A β-hairpin structure in a 13-mer peptide that binds α-bungarotoxin with high affinity and neutralizes its toxicity. Proc Natl Acad Sci U S A. Jun. 5, 2001;98(12):6629-34.*
(Continued)

*Primary Examiner* — Marcela M Cordero Garcia
*Assistant Examiner* — Jia-Hai Lee
(74) *Attorney, Agent, or Firm* — Clark & Elbing LLP

(57) ABSTRACT

The present invention deals with a bipodal-peptide binder that specifically binds with a target including (a) a structure stabilizing region that includes parallel, antiparallel or parallel and antiparallel amino acid strands wherein interstrand non-covalent bonds are formed; and (b) a target binding region I and a target binding region II that are bonded at both terminals of said structure stabilizing region and respectively include n and m amino acids, and a method of preparing same; the bipodal-peptide binder of the present invention exhibits the KD value (dissociation constant) of a very low level (for example, nM level) and, therefore, exhibits very high affinity toward a target. The bipodal-peptide binder of the present invention has applications not only in pharmaceuticals but also in in-vivo imaging, in vitro cell imaging, and drug delivery targeting, and can be very usefully employed as an escort molecule.

10 Claims, 23 Drawing Sheets
Specification includes a Sequence Listing.

Bipodal-peptide binder

(58) Field of Classification Search
CPC ............... C07K 14/001; C07K 1/1075; C07K 2319/00; C07K 2317/64; C07K 2317/76; C07K 2319/01; C07K 2319/70; A61K 38/00; A61K 2039/6031

See application file for complete search history.

(56) References Cited

U.S. PATENT DOCUMENTS

| | | | | |
|---|---|---|---|---|
| 5,885,577 A | * | 3/1999 | Alvarez | C07K 1/047 424/141.1 |
| 6,914,123 B2 | | 7/2005 | Cochran et al. | |
| 2003/0103978 A1 | | 6/2003 | Deshpande et al. | |
| 2003/0175700 A1 | | 9/2003 | Bhatia et al. | |
| 2003/0175799 A1 | | 9/2003 | Cochran et al. | |
| 2005/0196810 A1 | * | 9/2005 | Cochran et al. | 435/7.1 |
| 2008/0181886 A1 | | 7/2008 | Kelley | |
| 2012/0309934 A1 | | 12/2012 | Jon et al. | |
| 2012/0321697 A1 | | 12/2012 | Jon et al. | |

OTHER PUBLICATIONS

Lee at al. Understanding beta-hairpin formation by molecular dynamics simulations of unfolding. Biophys J. Nov. 2011;81(5):2507-16.*

Dias et al. Protein Ligand Design: From Phage Display to Synthetic Protein Epitope Mimetics in Human Antibody Fc-Binding Peptidomimetics. J. Am. Chem. Soc. 2006, 128, 2726-2732.*

Andersen et al. Minimization and Optimization of Designed β-Hairpin Folds. J. Am. Chem. Soc. 2006, 128, 6101-6110.*

Pasqualini et al. A Peptide Isolated from Phage Display Libraries Is a Structural and Functional Mimic of an RGD-binding Site on Integrins. J Cell Biol. Sep. 1995;130(5):1189-96.*

Junker et al. Single-molecule force spectroscopy distinguishes target binding modes of calmodulin. Proc Natl Acad Sci U S A. Aug. 25, 2009;106(34):14361-6.*

Liu et al. Function and solution structure of Huwentoxin-X, a specific blocker of N-type calcium channels, from the Chinese bird spider *Ornithoctonus huwena*. J. Biol. Chem. 2006, 281:8628-8635.*

Estrada et al. Spider venoms: a rich source of acylpolyamines and peptides as new leads for CNS drugs. Nat. Prod. Rep., 2007, 24, 145-161.*

Sharon et al. Alternative Conformations of HIV-1 V3 Loops Mimic β Hairpins in Chemokines, Suggesting a Mechanism for Coreceptor Selectivity. Structure. Feb. 2003;11(2):225-36.*

Barry et al. Toward cell-targeting gene therapy vectors: selection of cell-binding peptides from random peptide-presenting phage libraries. Nat Med. Mar. 1996;2(3):299-305.*

Martin et al. The affinity-selection of a minibody polypeptide inhibitor of human interleukin-6. EMBO J. Nov. 15, 1994;13(22):5303-9.*

Russell et al. Stability of Cyclic beta-Hairpins: Asymmetric Contributions from Side Chains of a Hydrogen-Bonded Cross-Strand Residue PairJ. Am. Chem. Soc. 2003, 125, 388-395.*

Boutillon et al. Synthesis, three-dimensional structure, and specific 15N-labelling of the streptococcal protein G B1-domain. Eur. J. Biochem. 1995; 231: 166-180.*

Hoogenboom et al. Natural and designer binding sites made by phage display technology. Immunol Today. Aug. 2000;21(8):371-8.*

Gupta et al. Intracellular delivery of large molecules and small particles by cell-penetrating proteins and peptides. Advanced Drug Delivery Reviews 57 (2005) 637-651.*

Skelton et al. Amino Acid Determinants of b-Hairpin Conformation in Erythropoeitin Receptor Agonist Peptides Derived from a Phage Display Library. J. Mol. Biol. (2002) 316, 1111-1125.*

Cheng et al. In Vivo Screening Identifies a Highly Folded b-Hairpin Peptide with a Structured Extension. ChemBioChem 2007, 8, 880-883.*

Bagalkot et al., "An Aptamer-Doxorubicin Physical Conjugate as a Novel Targeted Drug-Delivery Platform," Angew. Chem. Int. Ed. 45:8149-8152, 2006.

Clackson et al., "Making Antibody Fragments Using Phage Display Libraries," Nature 352:624-628, 1991.

International Search Report from International Application No. PCT/KR2009/006059, dated May 31, 2010.

U.S. Appl. No. 13/515,026, filed Aug. 16, 2012, Jon et al.

U.S. Appl. No. 13/515,163, filed Aug. 27, 2012, Jon et al.

PCT/KR2009/006059, May 31, 2010, International Search Report and Written Opinion.

PCT/KR2009/006059, May 5, 2011, International Preliminary Report on Patentability.

International Search Report and Written Opinion dated May 31, 2010 in connection with PCT/KR2009/006059.

International Preliminary Report on Patentability dated May 5, 2011 in connection with PCT/KR2009/006059.

Baldauf et al., Stable hairpins with beta-peptides: route to tackle protein-protein interactions. J Phys Chem B. Jun. 26, 2008;112(25):7581-91. doi:10.1021/jp076838r.

Butterfield et al., Minimalist protein design: a beta-hairpin peptide that binds ssDNA. J Am Chem Soc. Jan. 12, 2005;127(1):24-5.

Cochran et al., Tryptophan zippers: stable, monomeric beta-hairpins. Proc Natl Acad Sci U S A. May 8, 2001;98(10):5578-83. Erratum in: Proc Natl Acad Sci U S A Jun. 25, 2002;99(13):9081.

De Kruif et al., Leucine zipper dimerized bivalent and bispecific scFv antibodies from a semi-synthetic antibody phage display library. J Biol Chem. Mar. 29, 1996;271(13):7630-4.

Deechongkit et al., Beta-sheet folding mechanisms from perturbation energetics. Curr Opin Struct Biol. Feb. 2006;16(1):94-101. Review.

Dias et al., Protein ligand design: from phage display to synthetic protein epitope mimetics in human antibody Fc-binding peptidomimetics. J Am Chem Soc. Mar. 1, 2006;128(8):2726-32.

Fesinmeyer et al., Enhanced hairpin stability through loop design: the case of the protein G B1 domain hairpin. J Am Chem Soc. Jun. 16, 2004;126(23):7238-43.

Ganguly et al., Pharmacokinetic analysis of polyamide nucleic-acid-cell penetrating peptide conjugates targeted against HIV-1 transactivation response element. Oligonucleotides. Sep. 2008;18(3):277-86. doi: 10.1089/oli.2008.0140.

GenBank Accession No. 2EVQ-A. GenBank Database. Andersen et al. Oct. 31, 2005.

Gupta et al., Intracellular delivery of large molecules and small particles by cell-penetrating proteins and peptides. Adv Drug Deliv Rev. Feb. 28, 2005;57(4):637-51. Review.

Guss et al., Structure of the IgG-binding regions of streptococcal protein G. EMBO J. Jul. 1986;5(7):1567-75.

Honda et al., 10 residue folded peptide designed by segment statistics. Structure. Aug. 2004;12(8):1507-18.

Hoshino et al., Prolonged and extensive IgG immunoreactivity after severe fluid-percussion injury in rat brain. Brain Res. Mar. 4, 1996;711(1-2):73-83.

Liu et al., Design of hybrid β-hairpin peptides with enhanced cell specificity and potent anti-inflammatory activity. Biomaterials. Jan. 2013;34(1):237-50. doi: 10.1016/j.biomaterials.2012.09.032.

Meier et al., Foldon, the natural trimerization domain of T4 fibritin, dissociates into a monomeric A-state form containing a stable beta-hairpin: atomic details of trimer dissociation and local beta-hairpin stability from residual dipolar couplings. J Mol Biol. Dec. 3, 2004;344(4):1051-69.

Mohanty et al., Abundant intracellular IgG in enterocytes and endoderm lacking FcRn. PLoS One. Jul. 29, 2013;8(7):e70863. doi: 10.1371/journal.pone.0070863.

Noy et al., Prediction of structural stability of short beta-hairpin peptides by molecular dynamics and knowledge-based potentials. BMC Struct Biol. May 29, 2008;8:27. doi: 10.1186/1472-6807-8-27.

Pirozzi et al., Identification of novel human WW domain-containing proteins by cloning of ligand targets. J Biol Chem. Jun. 6, 1997;272(23):14611-6.

(56) References Cited

OTHER PUBLICATIONS

Robinson et al., Properties and structure-activity studies of cyclic beta-hairpin peptidomimetics based on the cationic antimicrobial peptide protegrin I. Bioorg Med Chem. Mar. 15, 2005;13(6):2055-64.

Robinson, Beta-hairpin peptidomimetics: design, structures and biological activities. Acc Chem Res. Oct. 2008;41(10):1278-88. doi: 10.1021/ar700259k.

Venkatraman et al., Design of folded peptides. Chem Rev. Oct. 2001;101(10):3131-52. Review.

Weisser et al.,Applications of single-chain variable fragment antibodies in therapeutics and diagnostics. Biotechnol Adv. Jul.-Aug. 2009;27(4):502-20. doi:10.1016/j.biotechadv.2009.04.004. Review.

Williams et al., Contributions to the catalytic efficiency of enzymes, and the binding of ligands to receptors, from improvements in packing within enzymes and receptors. Methods Enzymol. 2004;380:3-19.

Zhang et al., Artificial polypeptide scaffold for protein immobilization. J Am Chem Soc. Jul. 27, 2005;127(29):10136-7.

\* cited by examiner

Bipodal-peptide binder

Peptide 1

| Ka(1/Ms) | Kd(1/s) | KD(M) |
|---|---|---|
| 3.8 e4 | 0.024 | 620nM |

Peptide 2

| Ka(1/Ms) | Kd(1/s) | KD(M) |
|---|---|---|
| 1.0 e4 | 8.0 e-4 | 75nM |

Peptide 3

| Ka(1/Ms) | Kd(1/s) | KD(M) |
|---|---|---|
| 3.9 e5 | 0.099 | 2.5uM |

Peptide 1

| Ka(1/Ms) | Kd(1/s) | KD(M) |
|---|---|---|
| 2.2 e5 | 0.013 | 60nM |

Peptide 2

| Ka(1/Ms) | Kd(1/s) | KD(M) |
|---|---|---|
| 3.5 e4 | 0.011 | 326nM |

Peptide 1

| Ka(1/Ms) | Kd(1/s) | KD(M) |
|---|---|---|
| 2.5 e5 | 0.02 | 115nM |

GB1m3

| Ka(l/Ms) | Kd(1/s) | KD(M) |
|---|---|---|
| 1.69e5 | 0.0119 | 70nM |

HP7

| Ka(l/Ms) | Kd(1/s) | KD(M) |
|---|---|---|
| 2.36e5 | 0.0197 | 84nM |

BIPODAL-PEPTIDE BINDER

CROSS-REFERENCE TO RELATED APPLICATIONS

This application is the U.S. national stage filing under 35 U.S.C. § 371 of international application PCT/KR2009/006059, filed Oct. 20, 2009, which claims benefit of Korean Patent Application 10-2008-0102648, filed Oct. 20, 2008.

BACKGROUND OF THE INVENTION

Field of the Invention

The present invention relates to a bipodal-peptide binder and a method for preparing the same.

Background of Technique

An antibody is an immunoglobulin protein as a serum protein which is produced by B cells, and specifically recognizes a particular region of foreign antigen to inactivate or incapacitate antigen. Using high-specification and high-affinity of antigen-antibody reaction and applying a variety of antibodies capable of discriminating 10 million antigens, numerous antibody products including diagnostics and therapeutics have been developed nowadays. Twenty one monoclonal antibodies have been approved by FDA until now, and antibodies such as Rituximab and Herceptin have been proved to have an excellent efficacy over 50% of subjects who exhibit no response to other therapies. In practice, the utilization of monoclonal antibodies results in successful clinic treatment including lymphoma, colorectal cancer or breast cancer. Whole market size of therapeutic antibodies might be evaluated to be in an annual average of 20% growth rate from 10 billion dollars in 2004 to 30 billion dollars in 2010 and predicted to be increased in a geometrical progression. There has been emerging focus on development of new drug using antibody because of: (a) short development period of drug; (b) economical investment cost; and (c) feasible prediction of adverse effects. Additionally, antibody as a herb medicine has no influence on a human body and is beneficial to a subject since it has half-life much longer than drugs with a low molecular weight. In spite of these availabilities, monoclonal antibodies may induce severe allergic or hypersensitive responses in human body due to recognition as a foreign antigen. Furthermore, clinical utilization of a monoclonal antibody with an anti-cancer activity has the following drawbacks: (a) high therapeutics cost due to high production cost; and (b) expensive licensing fees because intellectual property rights protect widespread techniques such as culture and purification method of antibodies.

To overcome these problems, it is earlier beginning to develop antibody alternatives in USA and EU. The antibody alternatives are designed as a recombinant protein having constant and variable domain like an antibody, of which the size is small and a particular region of a stable protein is replaced by random amino acid sequence, leading to produce a library, and the library is utilized for screening a target molecules to isolate a molecule with high affinity and excellent specificity. For example, it has been reported that avimer and affibody of antibody alternatives have a superior affinity to a target molecule in picomole level. Generally, the small-sized and stable antibody alternatives have been reported to penetrate into cancer cells in a feasible manner and to induce immune responses in a low level. First of all, the antibody alternatives may avoid antibody patent barriers and have excellent advantages such as (a) low production cost and (b) feasible massive purification from bacteria. Currently, 40 antibody alternatives have been known, and the example of antibody alternatives commercially attempted in ventures or international pharmaceuticals includes fibronectin type III domain, lipocalin, LDLR-A domain, crystalline, protein A, ankyrin repeat or BPTI protein, which have high affinity to a target molecule in the level of picomole. Of them, FDA clinic experiments for adnectin, avimer or Kunitz domain are on-going at present.

The present invention focused on a peptide-based antibody alternative different from conventionally protein-based antibody alternatives. Presently, peptides have been applied in a various manner to replace conventional antibody alternative therapeutics due to merits such as: (a) suitable pharmacokinetics; (b) massive production; (c) low cytotoxicity; (d) inhibition of antigenicity; and (e) low production cost. As a therapeutic drug, the advantage of peptide includes: (a) low production cost; (b) high safety and responsiveness; (c) relatively low patent royalty; (d) inhibition of antibody production against peptide in itself according to rare exposure on undesirable immune system; and (e) feasible modification and outstanding accuracy via synthesis. However, since most of peptides exhibits low affinity and specificity to a particular protein target compared with antibody, there is a drawback that they may be not utilized in several application fields. Therefore, it has been urgently demanded in the art to develop a novel peptide-based antibody alternative to overcome demerits of peptides. In this connection, the present inventors have made intensive studies to develop a peptide molecule capable of specifically binding a biological target molecule with high affinity. It should be expected as a technique capable of identifying a new drug with high affinity and specificity in a high-throughput manner using a peptide with low affinity reported about very numerous targets.

Throughout this application, various publications and patents are referred and citations are provided in parentheses. The disclosures of these publications and patents in their entities are hereby incorporated by references into this application in order to fully describe this invention and the state of the art to which this invention pertains.

DETAILED DESCRIPTION OF THE INVENTION

The present inventors have made intensive studies to develop a peptide capable of binding specifically to a biological target molecule with much higher affinity. As results, we have discovered that both termini of a structure stabilizing region having a relatively rigid peptide backbone are randomly linked to two peptides which are bound to a target molecule cooperatively, thereby obtaining a bipodal-peptide binder with much more enhanced binding activity and specificity.

Accordingly, it is an object of this invention to provide a method for preparing a bipodal-peptide binder.

It is another object of this invention to provide a bipodal-peptide binder which specifically binds to a biological target molecule.

It is still another object to this invention to provide a nucleic acid molecule encoding the bipodal-peptide binder.

It is still another object to this invention to provide a vector for expressing a bipodal-peptide binder.

It is further still another object to this invention to provide a transformant including a vector for expressing a bipodal-peptide binder.

Other objects and advantages of the present invention will become apparent from the following detailed description together with the appended claims and drawings.

In one aspect of this invention, there is provided a method for preparing a bipodal-peptide binder which binds to a target, comprising the steps of:

(a) providing a library of the bipodal-peptide binder comprising (i) a structure stabilizing region comprising a parallel amino acid strand, an antiparallel amino acid strand or a parallel and an antiparallel amino acid strands to induce interstrand non-covalent bonds; and (ii) a target binding region I and a target binding region II each binding to each of both termini of the structure stabilizing region, wherein the number of amino acid residues of the target binding region I is n and the number of amino acid residues of the target binding region II is m;

(b) contacting the target with the library; and (c) selecting the bipodal-peptide binder to bind to the target.

In another aspect of this invention, there is provided a bipodal-peptide binder which specifically binds to a target, comprising: (a) a structure stabilizing region comprising a parallel amino acid strand, an antiparallel amino acid strand or a parallel and an antiparallel amino acid strands to induce interstrand non-covalent bonds; and (b) a target binding region I and a target binding region II each binding to each of both termini of the structure stabilizing region, wherein the number of amino acid residues of the target binding region I is n and the number of amino acid residues of the target binding region II is m.

The present inventors have made intensive studies to develop a peptide capable of binding specifically to a biological target molecule with much higher affinity. As results, we have discovered that both terminals of a structure stabilizing region having a relatively rigid peptide backbone are randomly linked to two peptides which are bound to a target molecule cooperatively, thereby obtaining a bipodal-peptide binder with much more enhanced binding activity and specificity.

Basic strategy of this invention is to link peptides which are bound to both termini of a rigid peptide backbone. In this instance, the rigid peptide backbone functions to stabilize whole structure of a bipodal-peptide binder, and to reinforce that a target binding region I and a target binding region II are bound to a target molecule.

The structure stabilizing region capable of being utilized in the present invention includes a parallel amino acid strand, an antiparallel amino acid strand or a parallel and an antiparallel amino acid strands, and protein structure motifs in which non-covalent bonds are formed by an interstrand hydrogen bond, an electrostatic interaction, a hydrophobic interaction, a Van der Waals interaction, a pi-pi interaction, a cation-pi interaction or a combination thereof. Non-covalent bonds formed by an interstrand hydrogen bond, an electrostatic interaction, a hydrophobic interaction, a Van der Waals interaction, a pi-pi interaction, a cation-pi interaction or a combination thereof contributes to rigidity of a structure stabilizing region.

According to a preferable embodiment, the interstrand non-covalent bonds in the structure stabilizing region include a hydrogen bond, a hydrophobic interaction, a Van der Waals interaction, a pi-pi interaction or a combination thereof.

Alternatively, covalent bond may be involved in the structure stabilizing region. For example, disulfide bond in the structure stabilizing region permits to significantly enhance rigidity of the structure stabilizing region. Increase of rigidity caused by covalent bond is determined according to specificity and affinity of bipodal-peptide binder to a target.

According to a preferable embodiment, amino acid strands of the structure stabilizing region of the present invention are linked by a linker. The term "linker" used herein in the strand refers to a material which may link between strands. For instance, a turn sequence in a β-hairpin used as a structure stabilizing region functions as a linker, and a material (e.g., peptide linker) linking between both C-termini in leucine zipper used as a structure stabilizing region functions as a linker.

Linker may link a parallel amino acid strand, an antiparallel amino acid strand or a parallel and an antiparallel amino acid strands. For example, at least two strands (preferably, two strands) arranged according to a parallel type, at least two strands (preferably, two strands) arranged according to an antiparallel type or at least three strands (preferably, three strands) arranged according to a parallel and an antiparallel type are linked by a linker.

According to a preferable embodiment, the linker of the present invention includes a turn sequence or a peptide linker.

According to a preferable embodiment, the turn sequence of the present invention includes a β-turn, a γ-turn, an α-turn, a π-turn or a ω-loop (Venkatachalam CM (1968), Biopolymers, 6, 1425-1436; Nemethy G and Printz M R (1972), Macromolecules, 5, 755-758; Lewis P N et al., (1973), Biochim. Biophys. Acta, 303, 211-229; Toniolo C. (1980) CRC Crit. Rev. Biochem., 9, 1-44; Richardson J S. (1981), Adv. Protein Chem., 34, 167-339; Rose G D et al., (1985), Adv. Protein Chem., 37, 1-109; Milner-White E J and Poet R. (1987), TIBS, 12, 189-192; Wilmot CM and Thornton J M. (1988), J. Mol. Biol., 203, 221-232; Milner-White E J. (1990), J. Mol. Biol., 216, 385-397; Pavone V et al. (1996), Biopolymers, 38, 705-721; Rajashankar K R and Ramakumar S. (1996), Protein Sci., 5, 932-946). Most preferably, the turn sequence used in the present invention is a β-turn.

Example of β-turn used as a turn sequence includes preferably type I, type I', type II, type II', type III or type III' turn sequence, more preferably type I, type I', type II or type II' turn sequence, much more preferably type I' or type II' turn sequence, and most preferably, type I' turn sequence (B. L. Sibanda et al., J. Mol. Biol., 1989, 206, 4, 759-777; B. L. Sibanda et al., Methods Enzymol., 1991, 202, 59-82).

According to another preferable embodiment, the sequence capable of being used as a turn sequence in the present invention is disclosed in H. Jane Dyson et al., Eur. J. Biochem. 255:462-471(1998), which is incorporated herein by reference. The sequence capable of being used as a turn sequence in the present invention includes the following amino acid sequence: X-Pro-Gly-Glu-Val (SEQ ID NO:42); or Ala-X-Gly-Glu-Val (SEQ ID NO:43)(X represents any amino acid selected from 20 amino acids).

According to one embodiment of this invention, it is preferable that two strands arranged according to a parallel type or two strands arranged according to an antiparallel type are linked by a peptide linker in β-sheet or leucine zipper used as a structure stabilizing region in the present invention.

It is possible in the present invention to utilize any peptide linker known to those ordinarily skilled in the art. The sequence of a suitable peptide linker may be selected by considering the following factor: (a) potential to be applied to a flexible extended conformation; (b) inability to form secondary structure capable of interacting with a biological target molecule; (c) absence of a hydrophobic or charged residue which interacts with a biological target molecule. Preferable peptide linkers include Gly, Asn and Ser residue. In addition, other neutral amino acid such as Thr and Ala may be included in a linker sequence. The amino acid sequence suitable in a linker is disclosed in Maratea et al., Gene 40:39-46(1985); Murphy et al., Proc. Natl. Acad Sci. USA 83:8258-8562(1986); U.S. Pat. Nos. 4,935,233, 4,751, 180 and 5,990,275. Peptide linker sequence in the present invention may be composed of 1-50 amino acid residues.

According to a preferable embodiment, the structure stabilizing region of the present invention includes a β-hairpin motif, a β-sheet motif linked by a linker or a leucine-zipper motif linked by a linker, more preferably a β-hairpin motif or a β-sheet motif linked by a linker, and most preferably, a β-hairpin motif.

The term "β-hairpin" used herein means the most simple protein motif containing two β strands which are arranged each other in an antiparallel manner. Generally, two β strands in a β-hairpin are linked by a turn sequence.

Preferably, a turn sequence applied to a (β-hairpin includes type I, type I', type II, type II', type III or type III' turn sequence, more preferably type I, type I', type II or type II' turn sequence, much more preferably type I' or type II' turn sequence, and most preferably, type I' turn sequence. In addition, the following turn sequence may be utilized in a β-hairpin: X-Pro-Gly-Glu-Val (SEQ ID NO:42); or Ala-X-Gly-Glu-Val (SEQ ID NO:43) (X represents any amino acid selected from 20 amino acids).

According to an illustrative example of the present invention, a type I turn sequence includes Asp-Asp-Ala-Thr-Lys-Thr (SEQ ID NO:44), and a type I' turn sequence includes Glu-Asn-Gly-Lys (SEQ ID NO:45), and a type II turn sequence includes X-Pro-Gly-Glu-Val (SEQ ID NO:42); or Ala-X-Gly-Glu-Val (SEQ ID NO:43) (X represents any amino acid selected from 20 amino acids), and a type II' turn sequence includes Glu-Gly-Asn-Lys (SEQ ID NO:46) or Glu-D-Pro-Asn-Lys (SEQ ID NO:47).

A peptide with (β-hairpin conformation is well-known to those ordinarily skilled in the art, for example including tryptophan zipper motif disclosed in U.S. Pat. No. 6,914,123 and Andrea G. Cochran et al., PNAS, 98(10):5578-5583), template-immobilized β-hairpin mimetics in WO 2005/047503 and β-hairpin modifiers in U.S. Pat. No. 5,807,979. Besides, peptide with β-hairpin conformation is disclosed in Smith & Regan (1995) Science 270:980-982; Chou & Fassman (1978) Annu. Rev. Biochem. 47:251-276; Kim & Berg (1993) Nature 362:267-270; Minor & Kim (1994) Nature 367:660-663; Minor & Kim (1993) Nature 371:264-267; Smith et al. Biochemistry (1994) 33:5510-5517; Searle et al. (1995) Nat. Struct. Biol. 2:999-1006; Haque & Gellman (1997) J. Am. Chem. Soc. 119:2303-2304; Blanco et al. (1993) J. Am. Chem. Soc. 115:5887-5888; de Alba et al. (1996) Fold. Des. 1: 133-144; de Alba et al. (1997) Protein Sci. 6:2548-2560; Ramirez-Alvarado et al. (1996) Nat. Struct. Biol. 3:604-612; Stanger & Gellman (1998) J. Am. Chem. Soc. 120:4236-4237; Maynard & Searle (1997) Chem. Commun. 1297-1298; Griffiths-Jones et al. (1998) Chem. Commun. 789-790; Maynard et al. (1998) J. Am. Chem. Soc. 120:1996-2007; and Blanco et al. (1994) Nat. Struct. Biol. 1:584-590, which are incorporated herein by reference.

Most preferably, a peptide with β-hairpin conformation as a structure stabilizing region utilizes a tryptophan zipper motif.

According to a preferable embodiment, the tryptophan zipper used in the present invention is represented by the following Formula I:

$X_1$-Trp($X_2$)$X_3$-$X_4$-$X_5$($X'_2$)$X_6$-$X_7$ (SEQ ID NO:48)   Formula I wherein $X_1$ represents Ser or Gly-Glu, and $X_2$ and $X'_2$ independently represent Thr, His, Val, Ile, Phe or Tyr, and $X_3$ represents Trp or Tyr, and $X_4$ represents type I, type I', type II, type II', type III or type III' turn sequence, and $X_5$ represents Trp or Phe, and $X_6$ represents Trp or Val, and $X_7$ represents Lys or Thr-Glu.

More preferably, $X_1$ represents Ser or Gly-Glu, and $X_2$ and $X'_2$ independently represent Thr, His or Val, and $X_3$ represents Trp or Tyr, and $X_4$ represents type I, type I', type II or type II' turn sequence, and $X_5$ represents Trp or Phe, and $X_6$ represents Trp or Val, and X, represents Lys or Thr-Glu in the Formula I.

Much more preferably, $X_1$ represents Ser or Gly-Glu, and $X_2$ and $X'_2$ independently represent Thr, His or Val, and $X_3$ represents Trp, and $X_4$ represents type I, type I', type II or type II' turn sequence, and $X_5$ represents Trp, and $X_6$ represents Trp, and $X_7$ represents Lys or Thr-Glu in the Formula I.

Still much more preferably, $X_1$ represents Ser, and $X_2$ and $X'_2$ represent Thr, and $X_3$ represents Trp, and $X_4$ represents type I' or type II' turn sequence, and $X_5$ represents Trp, and $X_6$ represents Trp, and X, represents Lys in the Formula I.

Most preferably, $X_1$ represents Ser, and $X_2$ and $X'_2$ represent Thr, and $X_3$ represents Trp, and $X_4$ represents type I' turn sequence (ENGK; SEQ ID NO:49) or type II' turn sequence (EGNK; SEQ ID NO:50), and $X_5$ represents Trp, and $X_6$ represents Trp, and $X_7$ represents Lys in the Formula I.

An illustrative amino acid sequence of tryptophan zipper suitable in the present invention is described in SEQ ID NOs:1-3 and SEQ ID NOs:5-10.

Another β-hairpin peptide capable of being utilized as a structure stabilizing region in the present invention includes a peptide derived from B1 domain of protein G, i.e. GB1 peptide.

Preferably, the GB1 peptide as a structure stabilizing region used in the present invention is represented by the following Formula II:

$X_1$-Trp-$X_2$-Tyr-$X_3$-Phe-Thr-Val-$X_4$ (SEQ ID NO:51)   Formula II wherein $X_1$ represents Arg, Gly-Glu or Lys-Lys, and $X_2$ represents Gln or Thr, and $X_3$ represents type I, type I', type II, type II', type III or type III' turn sequence, and $X_4$ represents Gln, Thr-Glu or Gln-Glu.

More preferably, the structure stabilizing region in the Formula II is is represented by the following Formula II':

$X_1$-Trp-Thr-Tyr-$X_2$-Phe-Thr-Val-$X_3$ (SEQ ID NO:52)   Formula II' wherein $X_1$ represents Gly-Glu or Lys-Lys, and $X_2$ represents type I, type I', type II, type II', type III or type III' turn sequence, and $X_3$ represents Thr-Glu or Gln-Glu.

An exemplified amino acid sequence of GB1 β-hairpin suitable in the present invention is described in SEQ ID NO:4 and SEQ ID NOs:14-15.

Beta-hairpin peptide capable of being utilized as a structure stabilizing region in the present invention includes a HP peptide.

Preferably, the HP peptide as a structure stabilizing region used in the present invention is represented by the following Formula III:

$X_1$-$X_2$-$X_3$-Trp-$X_4$-$X_5$-Thr-$X_6$$X_7$(SEQ ID NO:53)   Formula III wherein X₁ represents Lys or Lys-Lys, and X₂ represents Trp or Tyr, and X₃ represents Val or Thr, and X₄ represents type I, type I', type II, type II', type III or type III' turn sequence, and X₅ represents Trp or Ala, and X₆ represents Trp or Val, and X₇ represents Glu or Gln-Gln.

Still another β-hairpin peptide capable of being utilized as a structure stabilizing region in the present invention is represented by the following Formula IV:

X₁-X₂-X₃-Trp-X₄ (SEQ ID NO:54)　　　　Formula IV wherein X₁ represents Lys-Thr or Gly, and X₂ represents Trp or Tyr, and X₃ represents type I, type I', type II, type II', type III or type III' turn sequence, and X₄ represents Thr-Glu or Gly.

An illustrative amino acid sequence of β-hairpin in Formula III and IV is described in SEQ ID NOs:11-12, SEQ ID NO:15 and SEQ ID NOs:16-19.

According to the present invention, a β-sheet linked by a linker may be used as a structure stabilizing region. The structure of β-sheet includes an extended form of two strands arranged in a parallel or antiparallel manner, preferably in an antiparallel manner, and hydrogen bond is formed between two strands.

Both adjacent termini of two amino acid strands in a β-sheet structure are linked by a linker. As described above, various turn-sequences or peptide linkers may be utilized as a linker. Using a turn sequence as a linker, it is most preferable to utilize a β-turn sequence.

According to another modified embodiment, a leucine zipper motif or a leucine zipper motif linked by a linker may be used as a structure stabilizing region. Leucine zipper motif is a conservative peptide domain which causes a dimerization of two parallel α-chains and a dimerization domain found generally in a protein related to gene expression ("Leucine scissors". Glossary of Biochemistry and Molecular Biology (Revised). (1997). Ed. David M. Glick. London: Portland Press; Landschulz W H, et al. (1988) Science 240:1759-1764). In general, leucine zipper motif includes a haptad repeat sequence, and a leucine residue is located at fourth or fifth position. For example, a leucine zipper motif capable of being utilized in the present invention includes amino acid sequences such as LEALKEK, LKALEKE, LKKLVGE, LEDKVEE, LENEVAR and LLSKNYH. Practical example of leucine zipper motif used in the present invention is described in SEQ ID NO:39. Half of each leucine zipper motif is composed of a short α-chain, and includes direct leucine interaction between α-chains. In general, leucine zipper motif in a transcription factor consists of a hydrophobic leucine zipper region and basic region (a region interacting with a major groove of DNA molecule). A basic region is not necessary for the leucine zipper motif used in the present invention. In the structure of leucine zipper motif, both adjacent termini of two amino acid strands (i.e., two α-chains) may be linked by a linker. As described above, various turn-sequences or peptide linkers may be utilized as a linker. It is preferable to utilize a peptide linker which has no influence on the structure of leucine zipper motif.

Random amino acid sequence is linked in both termini of the above-mentioned structure stabilizing region. The random amino acid sequence forms a target binding region I and a target binding region II. It is one of the most features of the present invention that a peptide binder is constructed by a bipodal type which a target binding region I and a target binding region II are linked to both termini of a structure stabilizing region, respectively. The target binding region I and the target binding region II bind in a cooperative manner to a target, leading to enhance significantly affinity to the target.

The number (n) of amino acid residues of a target binding region I is not particularly limited, and is an integer of preferably 2-100, more preferably 2-50, much more preferably 2-20 and most preferably, 3-10.

The number (m) of amino acid residues of a target binding region II is not particularly limited, and is an integer of preferably 2-100, more preferably 2-50, much more preferably 2-20 and most preferably, 3-10.

The number of amino acid residuce of a target binding region I and a target binding region II may be independently different or equivalent. The amino acid sequence of a target binding region I and a target binding region II may be independently different or equivalent, and preferably independently different.

A sequence contained in a target binding region I and/or a target binding region II includes linear or circular amino acid sequence. To enhance stability of peptide sequence in the target binding regions, at least one amino acid residues of amino acid sequence contained in a target binding region I and/or a target binding region II may be modified into an acetyl group, a fluorenyl methoxy carbonyl group, a formyl group, a palmitoyl group, a myristyl group, a stearyl group or a polyethyleneglycol (PEG).

The bipodal-peptide binder of the present invention bound to a biological target molecule may be utilized in: (a) regulation of in vivo physiological response; (b) detection of in vivo material; (c) in vivo molecule imaging; (d) in vitro cell imaging; (e) targeting for drug delivery; and (f) escort molecule.

According to a preferable embodiment, a structure stabilizing region, a target binding region I or a target binding region II (more preferably, a structure stabilizing region and much more preferably, a linker of a structure stabilizing region) further includes a functional molecule. Example of the functional molecule includes a label capable of generating a detectable signal, a chemical drug, a biodrug, a cell penetrating peptide (CPP) and a nanoparticle, but not limited to.

The label capable of generating a detectable signal includes, but is not limited to, T1 contrast materials (e.g., Gd chelate compounds), T2 contrast materials [e.g., superparamagnetic materials (example: magnetite, $Fe_3O_4$, $\gamma$-$Fe_2O_3$, manganese ferrite, cobalt ferrite and nickel ferrite)], radioactive isotope (example: $^{11}C$, $^{15}O$, $^{13}N$, $P^{32}$, $S^{35}$, $^{44}Sc$, $^{45}Ti$, $^{118}I$, $^{136}La$, $^{198}Tl$, $^{200}Tl$, $^{205}Bi$ and $^{206}Bi$), fluorescent materials (fluorescein, phycoerythrin, rhodamine, lissamine, and Cy3/Cy5), chemiluminescent materials, magnetic particles, mass labels and dense electron particle.

For example, the chemical drug includes an anti-flammatory agent, an analgesic, an anti-arthritic agent, an antispasmodic agent, an anti-depressant, an anti-psychotic agent, a sedative, an anti-anxiety drug, a drug antagonist, an anti-Parkinson's disease drug, a choline agonist, an anti-cancer drug, an anti-angiogenesis inhibitor, an immunosuppressive agent, an anti-viral agent, an antibiotics, an appetite depressant, an anti-choline agent, an anti-histamine agent, an anti-migraine medication, a hormone agent, a coronary, cerebrovascular or perivascular vasodilator, a contraceptive, an anti-thrombotic agent, a diuretic agent, an anti-hypertensive agent, a cardiovascular disease-related therapeutics, a beauty care-related component (e.g., an anti-wrinkle agent, a skin-aging inhibitor and a skin whitening agent), but not limited to.

The above-mentioned biodrug may be insulin, IGF-1 (insulin-like growth factor 1), growth hormone, erythropoietin, G-CSFs (granulocyte-colony stimulating factors), GM-CSFs (granulocyte/macrophage-colony stimulating factors), interferon-α, interferon-β, interferon-γ, interleukin-1α and 1β, interleukin-3, interleukin-4, interleukin-6, interleukin-2, EGFs (epidermal growth factors), calcitonin, ACTH (adrenocorticotropic hormone), TNF (tumor necrosis factor), atobisban, buserelin, cetrorelix, deslorelin, desmopressin, dynorphin A (1-13), elcatonin, eleidosin, eptifibatide, GHRH-II (growth hormone releasing hormone-II), gonadorelin, goserelin, histrelin, leuprorelin, lypressin, octreotide, oxytocin, pitressin, secretin, sincalide, terlipressin, thymopentin, thymosine α1, triptorelin, bivalirudin, carbetocin, cyclosporin, exedine, lanreotide, LHRH (luteinizing hormone-releasing hormone), nafarelin, parathyroid hormone, pramlintide, T-20 (enfuvirtide), thymalfasin, ziconotide, RNA, DNA, cDNA, antisense oligonucleotide and siRNA, but is not limited to.

The target binding region I and/or target binding region II may include an amino acid sequence capable of binding to various targets. The material to be targeted by the bipodal-peptide binder includes a biological target such as a biochemical material, a peptide, a polypeptide, a nucleic acid, a carbohydrate, a lipid, a cell and a tissue, a compound, a metal material or a non-metal material, and preferably, a biological target.

Preferably, the biological target to be bound with the target binding region includes a biochemical material, a peptide, a polypeptide, a glycoprotein, a nucleic acid, a carbohydrate, a lipid or a glycolipid.

For instance, a biochemical material to be bound with the target binding region includes various in vivo metabolites (e.g., ATP, NADH, NADPH, carbohydrate metabolite, lipid metabolite and amino acid metabolite).

An illustrative example of peptide or polypeptide to be bound with the target binding region includes, but is not limited to, an enzyme, a ligand, a receptor, a biomarker, a hormone, a transcription factor, a growth factor, an immunoglobulin, a signal transduction protein, a binding protein, an ionic channel, an antigen, an attachment protein, a structure protein, a regulatory protein, a toxic protein, a cytokine and a coagulation factor. In more detail, a target of a bipodal-peptide binder includes fibronectin extra domain B (ED-B), VEGF (vascular endothelial growth factor), VEGFR (vascular endothelial growth factor receptor), VCAM1 (vascular cell adhesion molecule-1), nAchR (Nicotinic acetylcholine receptor), HAS (Human serum albumin), MyD88, EGFR (Epidermal Growth Factor Receptor), HER2/neu, CD20, CD33, CD52, EpCAM (Epithelial Cell Adhesion Molecule), TNF-α (Tumor Necrosis Factor-α), IgE (Immunoglobulin E), CD11A (α-chain of lymphocyte function-associated antigen 1), CD3, CD25, Glycoprotein IIb/IIIa, integrin, AFP (Alpha-fetoprotein), β2M (Beta2-microglobulin), BTA (Bladder Tumor Antigens), NMP22, cancer antigen 125, cancer antigen 15-3, calcitonin, carcinoembryonic Antigen, chromogranin A, estrogen receptor, progesterone receptor, human chorionic gonadotropin, neuron-specific enolase, PSA (Prostate-Specific Antigen), PAP (Prostatic Acid Phosphatase) and thyroglobulin.

An exemplified example of nucleic acid molecule to be bound with the target binding region includes, but is not limited to, gDNA, mRNA, cDNA, rRNA (ribosomal RNA), rDNA(ribosomal DNA) and tRNA. An illustrative example of carbohydrate to be bound with the target binding region includes cellular carbohydrates such as monosaccharides, disaccharides, trisaccharides and polysaccharides, but is not limited to. An exemplified example of lipid to be bound with the target binding region includes fatty acid, triacylglycerol, sphingolipid, ganglioside and cholesterol, but is not limited to.

The bipodal-peptide binder of the present invention may not only be linked to a biomolecule (e.g., protein) exposed on a cell surface but regulate an activity via binding to a biomolecule (e.g., protein) in a cell.

For targeting of cellular protein, it is preferable that the bipodal-peptide binder further includes a cell penetrating peptide (CCP).

The above-described CCP includes various CCPs known to those ordinarily skilled in the art, for example HIV-1 tat protein, Tat peptide analogues (e.g., oligoarginine), ANTP peptide, HSV VP22 transcriptional regulatory protein, MTS peptide derived from vFGF, penetratin, transportan or Pep-1 peptide, but is not limited to. The method to bind the CPP to the bipodal-peptide of the present invention may be carried out according to various methods known to those skilled in the art, for example covalently binding CPP to lysine residue of loop region in the structure stabilizing region of the present bipodal-peptide.

There are numerous target proteins which play a critical function in in vivo physiological activity, and the bipodal-peptide binder linked to CPP is penetrated into a cell and bound to these target proteins, contributing to regulation (e.g., suppression) of their activities. Example 19 as described below practically exemplifies a targeting of the bipodal-peptide binder of the present invention to a cellular protein. MyD88 is well known to interact with TLR 4, interleukin-1 receptor, RAC1, IRAK2 and IRAK1. CPP-bipodal-peptide binder with high binding specificity to MyD88 is penetrated into a cell to prevent MyD88 activity, leading to block expression of MMP-13 in an effective manner.

As described above, the bipodal-peptide binder of the present invention has a "N-target binding region I-one strand of structure stabilizing region-the other strand of structure stabilizing region-target binding region II-C" construct.

According to a preferable embodiment, the bipodal-peptide binder of the present invention includes a structure influence inhibiting region which blocks a structural interaction between target binding region and structure stabilizing region and is located at an interspace between target binding region I and one strand of structure stabilizing region and/or between and the other strand of structure stabilizing region and target binding region II. Rotation region of peptide molecule includes an amino acid which φ and ψ rotation are relatively free in peptide molecule. Preferably, an amino acid which φ and ψ rotation are relatively free is glycine, alanine and serine. The number of amino acid in the structure influence inhibiting region of the present invention may be used in a range of 1-10, preferably 1-8 and more preferably 1-3.

A library of the bipodal-peptide binder of the present invention having the above-described construct may be obtained according to various methods known in the art. The bipodal-peptide binder in the library has random sequence. The term "random sequence" used herein means that no sequence preference or no determined (or fixed) amino acid sequence is placed at any position of target binding region I and/or target binding region II.

For example, the library of the bipodal-peptide binder may be constructed according to split-synthesis method (Lam et al. (1991) Nature 354:82; WO 92/00091) which is carried out on solid supporter (e.g., polystyrene or polyacrylamide resin).

According to a preferable embodiment, the library of the bipodal-peptide binder is constructed by a cell surface display method (e.g., phage display, bacteria display or yeast display). Preferably, the library of the bipodal-peptide binder is prepared by a display method based on plasmids, bacteriophages, phagemids, yeasts, bacteria, mRNAs or ribosomes.

Phage display is a technique displaying various polypeptides as proteins fused with coat protein on phage surface (Scott, J. K. and Smith, G. P. (1990) Science 249: 386; Sambrook, J. et al., Molecular Cloning. A Laboratory Manual, 3rd ed. Cold Spring Harbor Press (2001); Clackson and Lowman, Phage Display, Oxford University Press (2004)). Gene of interest is fused with gene III or gene VIII of filamentous phage (e.g., M13), thereby displaying random peptides.

Phagemid may be utilized in phage display. Phagemid is a plasmid vector which has a replication origin of bacteria (e.g., ColE1) and one copy of intergenic region of bacteriophage. DNA fragment cloned into the phagemid is proliferated as same as a plasmid.

Using a phage display method for constructing a library of a bipodal-peptide binder, a preferable embodiment of the present invention includes the steps of: (i) preparing a library of an expression vector including a fusion gene in which a gene encoding a phage coat protein (e.g., gene III or gene VIII coat protein of filamentous phage such as M13) is fused with a gene encoding a bipodal-peptide binder, and a transcriptional regulatory sequence (e.g., lac promoter) operatively linked to the fusion gene; (ii) introducing the library into a suitable host cell; (iii) displaying a fusion protein on the phage surface by culturing the host cell and forming a recombinant phage or a phagemid virus particle; (iv) binding the particle to a target molecule by contacting the virus particle with a biological target molecule; and (v) removing the particle unbound to the target molecule.

The method to construct and screen a peptide library using a phage display method is disclosed in U.S. Pat. Nos. 5,723,286, 5,432,018, 5,580,717, 5,427,908, 5,498,530, 5,770,434, 5,734,018, 5,698,426, 5,763,192 and 5,723,323.

The method to prepare an expression vector including a bipodal-peptide binder may be carried out according to the method known in the art. For example, expression vector may be prepared by inserting a bipodal-peptide binder into a public phagemid or phage vector (e.g., pIGT2, fUSE5, fAFF1, fd-CAT1, m663, fdtetDOG, pHEN1, pComb3, pComb8, pCANTAB 5E (Pharmacia), LamdaSurfZap, pIF4, PM48, PM52, PM54, fdH and p8V5).

Most phage display methods are carried out using filamentous phage. Additionally, a library of bipodal-peptide binder may be constructed using lambda phage display (WO 95/34683; U.S. Pat. No. 5,627,024), T4 phage display (Ren et al. (1998) Gene 215:439; Zhu (1997) CAN 33:534) and T7 phage display (U.S. Pat. No. 5,766,905).

The method to introduce a vector library into a suitable host cell may be performed according to various transformation methods, and most preferably, electroporation (See, U.S. Pat. Nos. 5,186,800, 5,422,272 and 5,750,373). The host cell suitable in the present invention includes gram-negative bacteria such as E coli which includes JM101, *E. coli* K12 strain 294, *E. coli* strain W3110 and *E. coli* XL-1Blue (Stratagene), but is not limited to. It is preferable that host cells are prepared as a competent cell before transformation (Sambrook, 3. et al., Molecular Cloning. A Laboratory Manual, 3rd ed. Cold Spring Harbor Press (2001)). In general, selection of transformed cells may be carried out by culturing cells in a medium containing antibiotics (e.g., tetracycline and ampicillin). Selected transformants are further cultured in the presence of helper phage to produce recombinant phages or phagemid virus particles. Suitable helper phage as described above includes, but is not limited to, Ex helper phage, M13-KO7, M13-VCS and R408.

Selection of virus particle binding to a biological target molecule may be carried out using a conventional biopanning process (Sambrook, J. et al., Molecular Cloning. A Laboratory Manual, 3rd ed. Cold Spring Harbor Press (2001); Clackson and Lowman, Phage Display, Oxford University Press(2004)).

Practical example of the bipodal-peptide binder of the present invention is described in SEQ ID NOs:20-38 and SEQ ID NOs:40-41.

In still another aspect of this invention, there is provided a nucleic acid molecule encoding the bipodal-peptide binder of the present invention.

In still another aspect of this invention, there is provided a vector for expressing a bipodal-peptide binder including the nucleic acid molecule encoding the bipodal-peptide binder of the present invention.

In further still another aspect of this invention, there is provided a transformant containing the vector for expressing a bipodal-peptide binder of the present invention.

The term "nucleic acid molecule" as used herein refers to a comprehensive DNA (gDNA and cDNA) and RNA molecule, and a nucleotide as a basic unit in the nucleic acid includes not only natural nucleotides but also analogues which a sugar or base are modified (Scheit, *Nucleotide Analogs*, John Wiley, New York (1980); Uhlman and Peyman, *Chemical Reviews*, 90:543-584 (1990)).

According to a preferable embodiment, the vector of the present invention includes not only the nucleic acid molecule encoding a bipodal-peptide binder but also a strong promoter (e.g., tac promoter, lac promoter, lacUV5 promoter, lpp promoter, $p_L^\lambda$ promoter, $p_R^\lambda$ promoter, racy promoter, amp promoter, recA promoter, SP6 promoter, trp promoter and T7 promoter, etc.) for transcription, a ribosome-binding site for translation, and transcription/translation termination sequence.

According to a preferable embodiment, the vector of the present invention further includes a signal sequence (e.g., pelB) at 5'-end of nucleic acid molecule encoding a bipodal-peptide binder. According to a preferable embodiment, the vector of the present invention further includes a tagging sequence (e.g., myc tag) to examine whether bipodal-peptide binder is suitably expressed on phage surface.

According to a preferable embodiment, the vector of the present invention includes a phage coat protein, preferably a gene encoding a gene III or gene VIII coat protein of filamentous phage such as M13. According to a preferable embodiment, the vector of the present invention includes a replication origin of bacteria (e.g., ColE1) and/or bacteriophage. In addition, the vector of the present invention includes an antibiotics-resistance gene known to those ordinarily skilled in the art as a selection marker, for example resistant genes against ampicillin, gentamycin, carbenicillin, chloramphenicol, streptomycin, kanamycin, geneticin, neomycin and tetracycline.

The transformant of the present invention preferably includes gram-negative bacteria such as *E. coli* which includes JM101, *E. coli* K12 strain 294, *E. coli* strain W3110 and *E. coli* XL-1Blue (Stratagene), but is not limited to. The procedure to deliver the present vector into a cell may be carried out according to various methods known to those ordinarily skilled in the art. For example, the transformation using a prokaryotic cell as a host may be performed according to a CaCl$_2$ method (Cohen, S. N. et al., *Proc. Natl. Acac. Sci. USA*, 9: 2110-2114 (1973)), a Hanahan method (Cohen, S. N. et al., *Proc. Natl. Acac. Sci. USA*, 9:2110-2114 (1973); and Hanahan, D. *J. Mol. Biol.*, 166: 557-580 (1983)) and an electroporation method (U.S. Pat. NOs. 5,186,800, 5,422,272 and 5,750,373).

The bipodal-peptide binder of the present invention exhibits the KD value (dissociation constant) of a very low level (for example, nM level) and, therefore, exhibits very high affinity toward a biological target molecule. As described in Examples below, the bipodal-peptide binder has about 102-105-fold (preferably, about 103-104-fold) affinity higher than a monopodal peptide binder. The bipodal-peptide binder of the present invention has applications not only in pharmaceuticals and detection of in vivo material but also in in vivo imaging, in vitro cell imaging, and drug delivery targeting, and can be very usefully employed as an escort molecule.

The features and advantages of the present invention will be summarized as follows:

(a) The present invention provides a bipodal-peptide binder containing a novel construct.

(b) The distal two target binding regions which are linked to each both termini of a structure stabilizing region in the bipodal-peptide binder of the present invention bind in a cooperative or synergetic manner to the target.

(c) In this connection, the bipodal-peptide binder of the present invention exhibits the KD value (dissociation constant) of a very low level (for example, nM level) and, therefore, exhibits very high affinity toward a biological target molecule.

(d) The bipodal-peptide binder of the present invention has applications not only in pharmaceuticals and detection of in vivo material but also in in vivo imaging, in vitro cell imaging, and drug delivery targeting, and can be very usefully employed as an escort molecule.

Figure 1A:
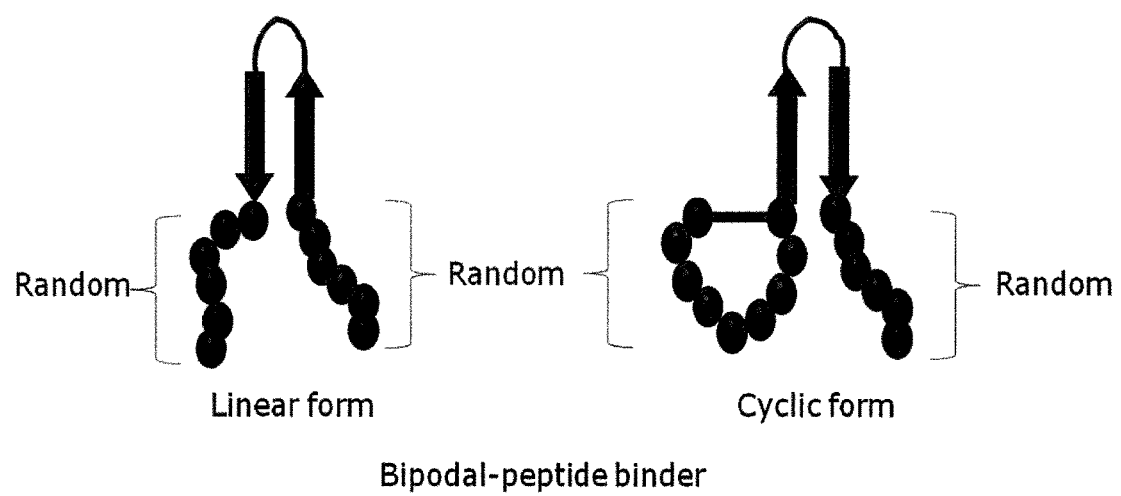
FIG. 1*a* schematically represents a bipodal-peptide binder containing a β-hairpin as a structure stabilizing region.
Figure 1B:
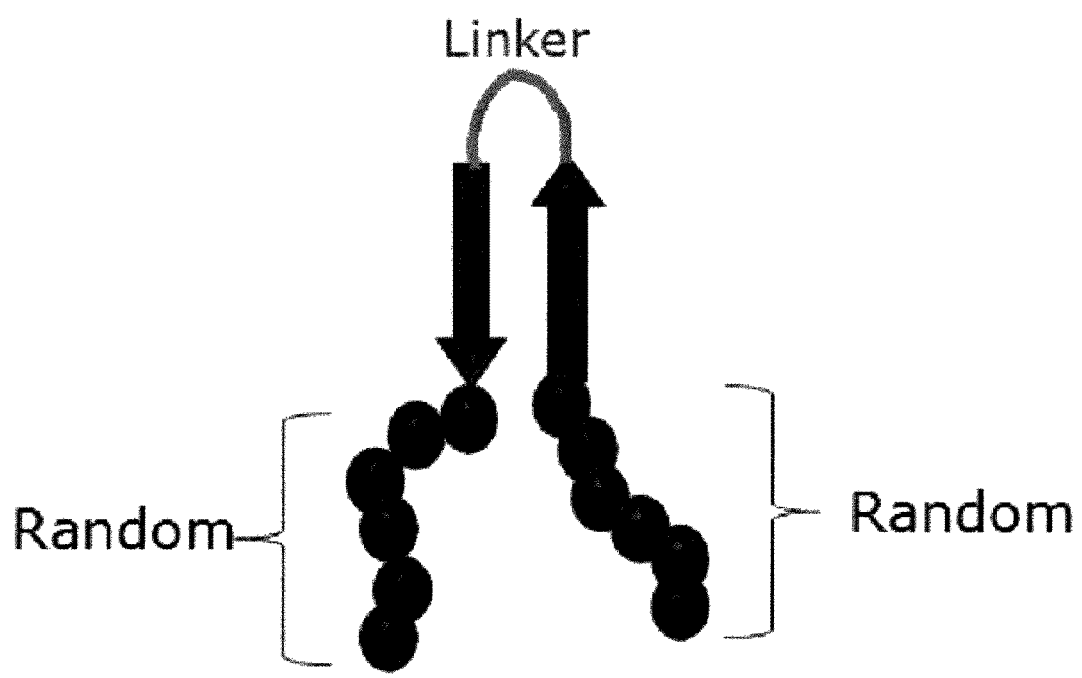
FIG. 1*b* schematically represents a bipodal-peptide binder containing a β-sheet linked by a linker as a structure stabilizing region.
Figure 1C:
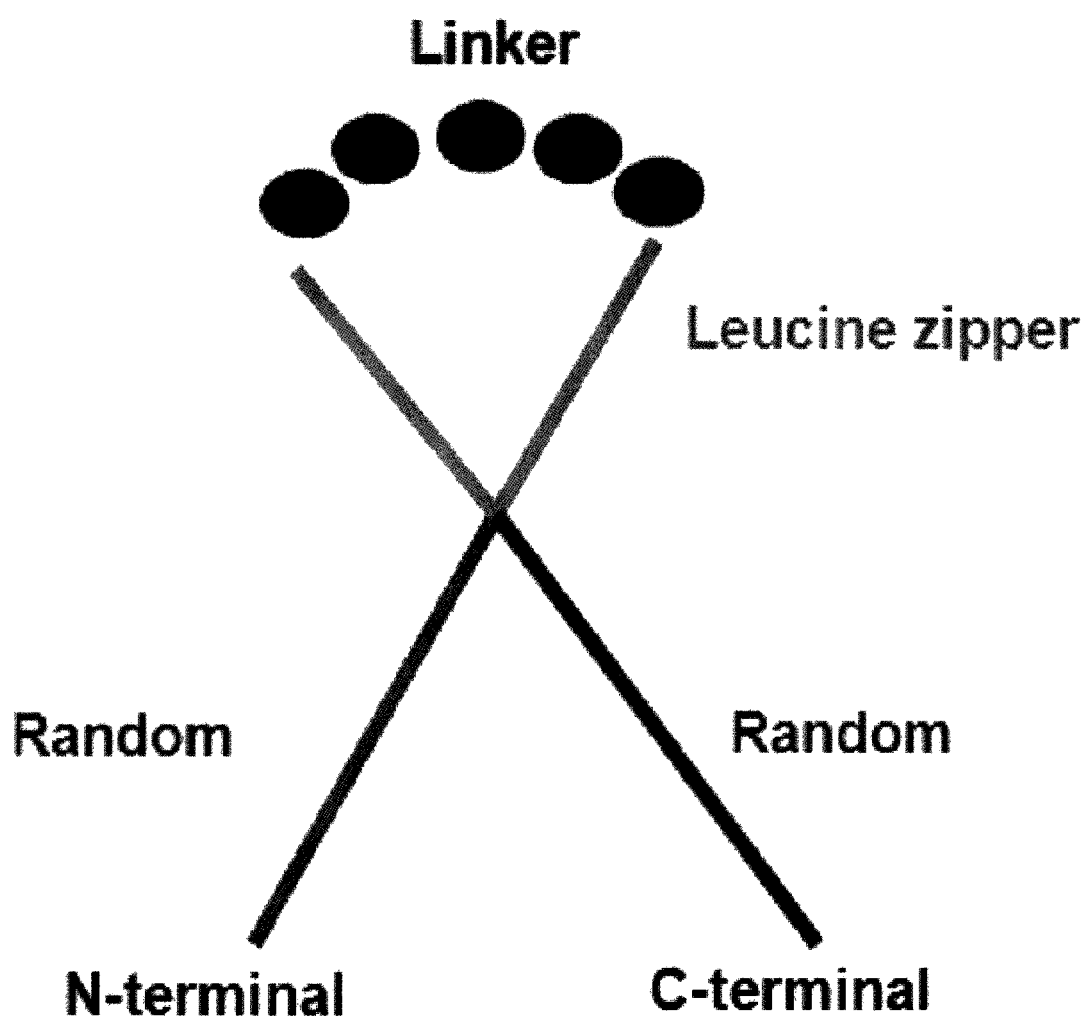
FIG. 1*c* schematically represents a bipodal-peptide binder containing a leucine zipper motif linked by a linker as a structure stabilizing region.
Figure 1D:
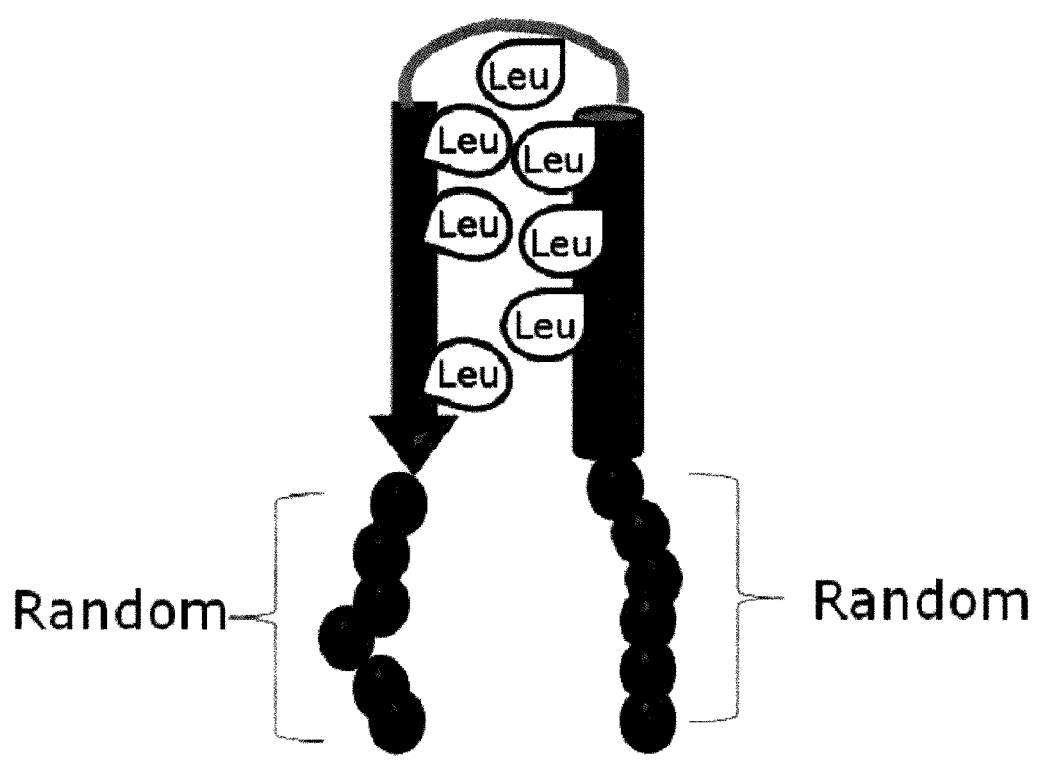
FIG. 1*d* schematically represents a bipodal-peptide binder containing a leucine-rich motif linked by a linker as a structure stabilizing region.

The present invention will now be described in further detail by examples. It would be obvious to those skilled in the art that these examples are intended to be more concretely illustrative and the scope of the present invention as set forth in the appended claims is not limited to or by the examples.

EXAMPLES

Experiment Material and Method

Example 1

Library Construction

Bipodal-peptide Binder (BPB) Gene Preparation and Insertion to Phargemid Vector

We synthesized two degenerate BPB-encoding oligonucleotides, BPB-F1 and BPB-B1, with the sequences 5'-TTCTATGCGGCCCAGCTGGCC (NNK)$_6$GGATCTTGGACATGGGAAAACGGAAAA-3' (SEQ ID NO:55) and 5'-AACAGTTTCTGCGGCCGCTCCTCCTCC (MNN)$_6$TCCCTTCCATGTCCATTTTCCGTT-3' (SEQ ID NO:56), respectively, where N is A, T, G or C; K is G or T; and M is C or A (Genotech). To synthesize double strand, Beta-F1(4 µM), Beta-B1 (4 µM), 2 µl dNTP mixture (2.5 mM), 1 µl ExTaq DNA polymerase (Takara, Seoul, Korea) and 10×PCR buffer were mixed and then distilled water was added to a final volume of 50 µl, preparing the mixture solution in total number of 25. After the double strand in the mixture was prepared by performing PCR (predenaturing step, 5 min at 94° C.; 60 cycles—30 sec at 94° C.; 30sec at 72° C.; and 7 min at 72° C.), the purification was carried out using PCR purification kit (GeneAll, Seoul, Korea), obtaining a bipodal-peptide binder (BPB) gene. To link the gene to be inserted into bipodal-peptide binder with pIGT2 phagemid vector (Ig therapy, Chuncheon, Korea), insert gene and pIGT2 phagemid vector were restricted with restriction enzyme. About 11 µg insert DNA were restricted with SfiI (New England Biolabs (NEB, Ipswich) and NotI (NEB, Ipswich) for 4 hrs, respectively, followed by purification using PCR purification kit. In addition, About 40 µg pIGT2 phargemid vector were restricted with SfiI and NotI for 4 hrs, respectively, and then CIAP (Calf Intestinal Alkaline Phosphatase; NEB, Ipswich) was treated for 1 hr, followed by purification using PCR purification kit. Both insert DNA and pGIT2 phargemid vector were quantitated using UV-visible light spectrophotometer (Ultrospec 2100pro, Amersham Bioscience), and 2.9 µg insert DNA were ligated with 12 µg pIGT2 phargemid vector at 18° C. for 15 hrs using T4 DNA ligase (Bioneer, Daejeon, Korea). After ethanol precipitation, DNA was dissolved in 100 µl TE buffer.

Competent Cell Preparation

E. coli XL1-BLUE (American Type Culture Collection, Manassas, USA) cells were linearly spread in LB agar-plate. The colony grown on solid agar media was inoculated into 5 ml LB media, and then incubated at 37° C. overnight with shaking at 200 rpm. The cells (10 ml) were inoculated into 2 liter of LB media, and cultured in the same manner until reaching at 0.3-0.4 of absorbance at 600 nm. The cultured flask was placed on ice for 30 min, and centrifuged at 4,000×g for 20 min at 4° C. The supernatant was completely removed, and the precipitated cells were suspended in 1 liter cold-sterile distilled water. After performing repeatedly as described above, the cells were resuspended in 1 liter cold-sterile distilled water. Also, after centrifugation and washing with 40 ml glycerol solution (10%), the cells were finally dissolved in 4 ml glycerol solution (10%) and aliquoted to 200 µl. Aliquots (200 µl) were freezed with liquid nitrogen, and stored at −80° C. until use.

Electroporation

Electroporation was carried out using 25 aliquots of 100 µl mixture in which 2.9 µg insert DNA are linked to 12 µg phagemid vector and a bipodal-peptide binder. After competent cells (200 µl) were dissolved on ice and mixed with 4 µl aliquot, the mixture was put into 0.2 cm cuvette and placed on ice for 1 min. Using an electroporator (BioRad, Hercules, Calif.) set the resistance at 200 Ω, the capacitance at 25 µF and the voltage to 2.5 kV, electric pulse (time constant, 4.5-5 msec) is applied to the cuvette. Immediately, the mixture was added to 1 ml LB liquid media containing 20 mM glucose to be pre-warmed at 37° C., and cells in total volume of 25 ml were obtained and then transferred into 100 ml test tube. After culturing at 200 rpm for 1 h at 37° C., 10 µl diluents were spread on ampicillin-agar media plate to count the number of library. The remaining cells were cultured overnight at 30° C. in 1 liter LB containing 20 mM glucose and 50 µg/ml ampicillin. After the supernatant was completely removed by centrifugation at 4,000×g for 20 min at 4° C. and the precipitated cells were resuspended in 40 ml LB media, the cells were finally dissolved in glycerol solution of not less than 20%, and stored at −80° C. until use.

Recombinant Phage Production from Library and PEG Precipitation

Recombinant phages were prepared from a bipodal-peptide binder library stored at −80° C. After 50 µg/ml ampicillin and 20 mM glucose were added to 100 ml LB liquid media in 500 ml flask, 1 ml library stored at −80° C. were inoculated into the media and then cultured at 150 rpm for 1 hr at 37° C. Afterwards, Ex helper phages (1×10$^{11}$ pfu/ml; Ig therapy, Chuncheon, Korea) were added to the media and cultured for 1 hr in the equal conditions. After removing the supernatant through centrifugation at 1,000×g for 10 min, the cells were incubated overnight in 100 ml LB liquid media supplemented with 50 µg/ml ampicillin and 25 µg/ml kanamycin to produce recombinant phages. After centrifuging the culture solution at 3,000×g for 10 min, 100 ml of the supernatant were mixed with 25 ml PEG/NaCl solution and kept to stand on ice for 1 hr. The supernatant was removed by centrifuging the culture solution at 10,000×g for 20 min at 4° C., and the pellet was resuspended in 2 ml PBS (pH 7.4).

Example 2

Protein Preparation

Fibronectin ED-B, VEGF (vascular endothelial growth factor), VCAM1 (vascular cell adhesion molecule-1), nAchR (Nicotinic acetylcholine receptor),HAS (Human serum albumin) and MyD88 to be used in the Examples were prepared as follows.

Fibronectin ED-B Gene Construction and Insertion into Expression Vector

Partial human fibronectin ED-B (ID=KU017225) gene were provided from Korea Research Institute of Bioscience & Biotechnology (KRIBB). We synthesized two primers, EDB_F1 (5'-TTCATAACATATGCCAGAGGTGC-CCCAA-3') (SEQ ID NO:57) and EDB_B1 (5'-ATTG-GATCCTTACGTTTGTTGTGTCAGTGTAGTAGGGGC-ACTCTCGCCGCCATTAATGAGAGTGATAACGCTGA-TATCATAGTCAATGCCCGGCTCCAGCCCTGTG-3') (SEQ ID NO:58). Twenty pmol EDB_F1, 20pmol EDB_B1, 4 µl dNTP mixture (2.5 mM), 1 µl ExTaq DNA polymerase (10 U) and 5 µl 10×PCR buffer were mixed and then distilled water was added to a final volume of 50 µl, preparing the mixture solution. After the EDB insert was prepared by performing PCR (pre-denaturing step, 5 min at 94° C.; 30 cycles—30 sec at 94° C.; 30 sec at 55° C.; and 1 min at 72° C.), and purified using PCR purification kit. To clone the insert into pET28b vector, EDB insert and pET28b vector were restricted with restriction enzyme. About 2 pg EDB insert were restricted with BamHI (NEB, Ipswich) and NdeI (NEB, Ipswich) for 4 hrs, followed by purification using PCR purification kit. In addition, About 2 µg pIGT2 phargemid vector were restricted with BamHI and NdeI for 3 hrs, respectively, and then CIAP was treated for 1 hr, followed by purification using PCR purification kit. The vector and insert were mixed at a molar ratio of 1:3 and ligated at 18° C. for 10 hrs using T4 DNA ligase (Bioneer, Daejeon, Korea). After transformation to-XL-1 competent cells, the transformed cells were spread in agar media containing kanamycin. The colony grown on a solid agar plate was inoculated into 5 ml LB media, and then incubated at 37° C. overnight with shaking at 200 rpm. Plasmids were purified by plasmid preparation kit (GeneAll, Seoul, Korea), and then sequenced to determine whether the cloning is successive.

VEGF121 Gene Construction and Insertion into Expression Vector

Partial human VEGF (ID=G157) gene were provided from Bank for Cytokine Research (BCR; Jeonju, Korea). We synthesized two primers, VEGF_F1 (5'-ATAGAATTCG-CACCCATGGCAGAA-3') (SEQ ID NO:59) and VEGF_B1 (5'-ATTAAGCTTTCACCGCCTCGGCTTGTCA-CAATTTTCTTGTCTTGC-3') (SEQ ID NO:60). Twenty pmol VEGF_F1, 20 pmol VEGF_B1, 4 µl dNTP mixture (2.5 mM), 1 µl ExTaq DNA polymerase (10 U) and 5 µl 10×PCR buffer were mixed and then distilled water was added to a final volume of 50 µl, preparing the mixture solution. After the VEGF insert was prepared by performing PCR (pre-denaturing step, 5 min at 94° C.; 30 cycles—30 sec at 94° C.; 30 sec at 55° C.; and 1min at 72° C.), and purified using PCR purification kit. To clone the insert into pET32a vector (Novagen), VEGF insert and pET32a vector were restricted with restriction enzyme. About 2 µg VEGF insert were restricted with EcoRI (NEB, Ipswich) and HindIII (NEB, Ipswich) for 4 hrs, followed by purification using PCR purification kit. The vector and insert were mixed at a molar ratio of 1:3 and ligated at 18° C. for 10 hrs using T4 DNA ligase (Bioneer, Daejeon, Korea). After transformation to XL-1 competent cells, the transformed cells were spread in agar media containing ampicillin. The colony grown on a solid agar plate was inoculated into 5 ml LB media, and then incubated at 37° C. overnight with shaking at 200 rpm. Plasmids were purified by plasmid preparation kit (GeneAll, Seoul, Korea), and then sequenced to determine whether the cloning is successive.

VCAM1 Gene Construction and Insertion into Expression Vector

Human VCAM gene was provided from Korea Research Institute of Bioscience & Biotechnology (KRIBB). To clone the insert into pET32a vector, VCAM1 insert and pET32a vector were restricted with restriction enzyme. The vector and insert were mixed at a molar ratio of 1:3 and ligated at 18° C. for 10 hrs using T4 DNA ligase (Bioneer, Daejeon, Korea). After transformation to XL-1 competent cells, the transformed cells were spread in agar media containing ampicillin. The colony grown on a solid agar plate was inoculated into 5 ml LB media, and then incubated at 37° C. overnight with shaking at 200 rpm. Plasmids were purified by plasmid preparation kit (GeneAll, Seoul, Korea), and then sequenced to determine whether the cloning is successive.

Expression and Purification Fibronectin ED-B

After transformation of pET28b vector carrying fibronectin ED-B into BL21 cells, the transformed cells were spread in agar media containing kanamycin. The colony grown on a solid agar plate was inoculated into 5 ml LB media containing kanamycin (25 µg/ml), and then incubated at 37° C. overnight with shaking at 200 rpm, followed by further incubation for 3 hrs in 50 ml of fresh LB media containing kanamycin (25 µg/ml). The cultured E. coli were inoculated into 2 liter of LB containing kanamycin (25 µg/ml) and then cultured to OD=0.6-0.8. Afterwards, 1 mM isopropyl-13-D-thiogalactopyranoside (IPTG) were added to the media and cultured at 37° C. for 8 hrs with shaking at 200 rpm. After removing the supernatant through centrifugation at 4,000×g for 20 min, the precipitated cells were suspended in lysis buffer [50 mM sodium phosphate (pH 8.0), 300 mM NaCl and 5 mM imidazole]. After storing at −80° C. overnight, E. coli were lysed using a sonicator and then centrifuged at 15,000×g for 1 hr, followed by binding the supernatant to Ni-NTA affinity resin (Elpisbio, Daejeon, Korea). After washing the resin with lysis buffer, N-terminal His-tag ED-B proteins were eluted with elution buffer [50 mM sodium phosphate (pH 8.0), 300 mM NaCl and 300 mM imidazole]. ED-B protein with high purity was obtained from the eluent by gel filtration using Superdex75 column (GE Healthcare, United Kingdom) and PBS (pH 7.4). For biopanning, biotin is conjugated to the ED-B protein. Six mg of sulfo-NHS-SS-biotin (PIERCE, Ill., USA) and 1.5 mg ED-B protein were incubated in 0.1 M sodium borate (pH 9.0) at room temperature for 2 hrs. To eliminate residual sulfo-NHS-SS-biotin, biotinylated-EDB protein was purified by gel filtration using Superdex75 column and PBS (pH 7.4).

Expression and Purification of VEGF121 and VCAM1-Trx

After transformation of pET32a vector carrying VEGF121 and VCAM1 into AD494 cells, the transformed cells were spread in agar media containing ampicillin, respectively. The colony grown on a solid agar plate was inoculated into 5 ml LB media containing ampicillin (25 µg/ml), and then incubated at 37° C. overnight with shaking at 200 rpm, followed by further incubation for 3 hrs in 50 ml of fresh LB media containing ampicillin (25 µg/ml). The cultured E. coli were inoculated into 2 liter of LB containing kanamycin (25 µg/ml) and then cultured to OD=0.6-0.8. Afterwards, 1 mM isopropyl-β-D-thiogalactopyranoside (IPTG) were added to the media and cultured at 37° C. for 8 hrs with shaking at 200 rpm. After removing the supernatant through centrifugation at 4,000×g for 20 min, the precipitated cells were suspended in lysis buffer [50 mM sodium phosphate (pH 8.0), 300 mM NaCl and 5 mM imidazole]. After storing at −80° C. overnight, E. coli were lysed using a sonicator and then centrifuged at 15,000×g for 1 hr, followed by binding the supernatant to Ni-NTA affinity resin (Elpisbio, Daejeon, Korea). After washing the resin with lysis buffer, Trx-VEGF121 and Trx-VCAM1 proteins were eluted with elution buffer [50 mM sodium phosphate (pH 8.0), 300 mM NaCl and 300 mM imidazole]. VEGF-Trx and VCAM1-Trx protein with high purity were obtained from the eluent by gel filtration using Superdex75 column (GE Healthcare, United Kingdom) and PBS (pH 7.4). For obtaining pure VEGF121 protein, VEGF-Trx was cut with thrombin.

Meanwhile, HAS was purchased from Genetex Inc. (Irvine).Biotin-SGEWVIKEARGWKHWVFYSC-CPTTPYLDITYH (32 mer) (SEQ ID NO:61), a peptide fragment of nAchR (Nicotinic acetylcholine receptor), was synthesized from Anigen Inc. (Korea, Kwangju). Human MyD88 was purchased from Santa Cruz Biotechnology (sc-4540 WB; California).

Example 3

Biopanning

Biopanning of Biotinylated-Fibronectin ED-B protein and Biotinylated-nAchR Peptide Two ml of straptavidin (10 μg/ml) were added to 40 wells (50 μl per well) in a 96-well ELISA plate and then kept to stand at 4° C. overnight. Next day, only 20 wells were washed with 0.1% PBST (tween-20) three times, and each biotinylated ED-B and biotinylated nAchR (10 μg/ml) was added and incubated at room temperature for 1 hr. Afterwards, all 40 wells were washed with 0.1% PBST (tween-20) three times and blocked at room temperature for 2 hrs using 2% BSA diluted with PBS. Then, the solution was removed and the plate was washed with 0.1% PBST three times. To eliminate streptavidin- and BSA-bound phages, the mixture of 800 μl solution containing bipodal-peptide binder recombinant phages and 200 μl BSA (10%) was added to 20 wells coated with streptavidin and BSA, and incubated at 27° C. for 1 hr. The supernatant collected was transferred to the well in which ED-B and nAchR was bound, and kept to stand at 27° C. for 45 min. The solution in 20 wells was completely removed and washed with 0.5% PBST 15 times in round 1. Bound phages were subsequently eluted for 20 min by adding 1 ml of 0.2 M glycine/HCl (pH 2.2) to each well (50 μl per well). The phages were collected in 1 ml tube and neutralized by adding 150 μl of 2 M Tris-base (pH 9.0). To measure the number of input and elute phage per biopanning, the phages were mixed with XL-1 BLUE cells (OD=0.7) and spread in agar plate containing ampicillin. To repeat panning, the phages were mixed with 10 ml $E.$ $coli$ XL1-BLUE cells and incubated at 37° C. for 1 hr with shaking at 200 rpm. After mixing with ampicillin (50 μg/ml) and 20 mM glucose, Ex helper phages ($2 \times 10^{10}$ pfu/ml) were added to the media and cultured at 37° C. for 1 hr with shaking at 200 rpm. After removing the supernatant through centrifugation at 1,000×g for 10 min, the precipitated cells were incubated at 37° C. overnight with shaking at 200 rpm in 40 ml LB liquid media supplemented with 50 μg/ml ampicillin and 25 μg/ml kanamycin. After centrifuging the culture solution at 4,000×g for 10 min at 4° C., the supernatant were mixed with 8 ml of 5×PEG/NaCl solution [20(w/v)% PEG and 15(w/v)% NaCl] and kept to stand at 4° C. for 1 hr. The supernatant was completely removed and the phage peptide pellet was resuspended in 1 ml PBS solution, which is used in $2^{nd}$ biopanning. Each biopanning step was carried out according to the same method as described above except for washing with 0.1% PBST 25 times in round 2 and 35 times in round 3.

Biopanning of VEGF and VCAM1-Trx and Human Serum Albumin (HSA), MyD88

VEGF and VCAM1-Trx and HSA and MyD88 (5 μg/ml) were added to 10 wells (50 μl per well) in a 96-well ELISA plate (Corning) and then kept to stand at 4° C. overnight. Next day, the wells were blocked at room temperature for 2 hrs with 2% BSA. Then, the solution was removed and the plate was washed with 0.1% PBST three times. The mixture of 800 μl solution containing bipodal-peptide binder recombinant phages and 200 μl BSA (10%) was added to 10 wells which VEGF and VCAM1-Trx and HSA were bound, and incubated at room temperature for 1 hr. The solution in 10 wells was completely removed and washed with 0.1% PBST 10 times in round 1. Bound phages were subsequently eluted for 20 min by adding 1 ml of 0.2 M glycine/HCl (pH 2.2) to each well (50 μl per well). The phages were collected in 1 ml tube and neutralized by adding 150 μl of 2 M Tris-base (pH 9.0). To measure the number of input and elute phage per biopanning, the phages were mixed with XL-1 BLUE cells (OD=0.7) and spread in agar plate containing ampicillin. To repeat panning, the phages were mixed with 10 ml $E.$ $coli$ XL1-BLUE cells and incubated at 37° C. for 1 hr with shaking at 200 rpm. After mixing with ampicillin (50 μg/ml) and 20 mM glucose, Ex helper phages ($2 \times 10^{10}$ pfu/ml) were added to the media and cultured at 37° C. for 1 hr with shaking at 200 rpm. After removing the supernatant through centrifugation at 1,000×g for 10 min, the precipitated cells were incubated at 37° C. overnight with shaking at 200 rpm in 40 ml LB liquid media supplemented with 50 μg/ml ampicillin and 25 μg/ml kanamycin. After centrifuging the culture solution at 4,000×g for 10 min at 4° C., the supernatant were mixed with 8 ml of 5×PEG/NaCl solution [20(w/v)% PEG and 15(w/v)% NaCl] and kept to stand at 4° C. for 1 hr. The supernatant was completely removed and the phage peptide pellet was resuspended in 1 ml PBS solution, which is used in $2^{nd}$ biopanning. Each biopanning step was carried out according to the same method as described above except for washing with 0.1% PBST 20 times in round 2 and 30 times in round 3.

Example 4

ELISA of Input Phage to Fibronectin ED-B

To investigate specificity, ELISA of each input phage of bipodal-peptide binder library was carried out for streptavidin, BSA and ED-B. Each straptavidin (10 μg/ml) and BSA (10 μg/ml) was added to 18 wells (50 μl per well) and 9 wells (50 μl per well) in a 96-well ELISA plate and then kept to stand at 4° C. overnight. Next day, only 9 wells of 18 wells containing streptavidin were washed with 0.1% PBST (tween-20) three times, and biotinylated ED-B (10 μg/ml) was added and incubated at room temperature for 1 hr. Afterwards, all wells were washed with 0.1% PBST (tween-20) three times and blocked at room temperature for 2 hrs using 2% BSA diluted with PBS. Then, the solution was removed and the plate was washed with 0.1% PBST three times. Each 800 μl of first, second and third phage solution containing bipodal-peptide binder recombinant phages and 200 μl BSA (10%) was mixed. Then, 100 μl of mixture was added to 3 wells coated with ED-B, streptavidin and BSA, respectively, and incubated at 27° C. for 1.5 hrs. After washing with 0.1% PBST 10 times, HRP-conjugated anti-M13 antibodies (1:1,000 dilution; GE Healthcare) were added to each well and incubated at 27° C. for 1 hr. After washing with 0.1% PBST 5 times, 100 μl tetramethylbenzidine (TMB; BD Science) as a substrate of peroxidase was seeded into each well to induce colorimetric reaction, followed by stopping the reaction adding 100 μl of 1 M HCl. The absorbance was measured at 450 nm.

Example 5

Detection of Phage Peptide Specific to Fibronectin ED-B, VEGF, VCAM1, nAchR, HAS and MyD88 protein (Phage ELISA)

XL1-BLUE cells were transformed with phages recovered from biopanning step having the highest ratio of output phage to input phage, and spread in plate to produce 100-200 of plaques. Using a sterile tip, 60 plaques were inoculated in 2 ml LB-ampicillin (50 μg/ml) media and cultured at 37° C. for 5 hr with vigorous shaking. The transformed cells were infected with Ex helper phages ($5 \times 10^9$ pfu/ml; OD=0.8-1.0)

and cultured at 37° C. for 1 hr with shaking at 200 rpm. After removing the supernatant by centrifuging at 1,000×g for 10 min, the precipitated cells were resuspended in 1 ml LB liquid media supplemented with 50 µg/ml ampicillin and 25 µg/ml kanamycin, and cultured at 30° C. overnight with shaking at 200 rpm. The supernatant was collected by centrifuging at 10,000×g for 20 min at 4° C. and mixed with 2% skim milk, which is used in detection of phage peptides.

Fibronectin ED-B, VEGF, VCAM1, Nicotinic acetylcholine receptor (nAchR), Human serum albumin and MyD88 (each 5 µg/ml) and BSA (10 µg/ml) were added to 30 wells (50 µl per well) in a 96-well ELISA plate and then kept to stand at 4° C. overnight. Next day, all wells were washed with 0.1% PBST three times, and blocked at room temperature for 2 hrs using 2% skim milk diluted with PBS. Then, the solution was removed and the plate was washed with 0.1% PBST three times. Phage peptide solution (100 µl) amplified from each clone was divided into all wells and kept to stand at 27° C. for 1.5 hrs. After washing with 0.1% PBST 5 times, HRP-conjugated anti-M13 antibodies (1:1, 000 dilution; GE Healthcare) were added to each well and incubated at 27° C. for 1 hr. After washing with 0.1% PBST 5 times, 100 µl TMB was divided into each well to induce colorimetric reaction, followed by stopping the reaction adding 100 µl of 1 M HCl. The absorbance was measured at 450 nm to select phages which had the absorbance higher than BSA. XL1 cells were infected with these phages and spread in plate to produce 100-200 of plaques. Using a sterile tip, plaques were inoculated in 4 ml LB-ampicillin (50 µg/ml) media and cultured at 37° C. overnight with vigorous shaking. Plasmids were purified by plasmid preparation kit (GeneAll, Seoul, Korea), and then sequenced. The following phagemid sequence was used for sequencing: 5'-GATTACGCCAAGCTTTGGAGC-3' (SEQ ID NO:62).

Example 6

Phage Peptide Specific to Fibronectin ED-B, VEGF or nAchR Binding Assay

Bipodal-peptide binder peptides specific to ED-B, VEGF or nAchR which were repetitively found in DNA sequencing were synthesized from Anigen Inc. (Korea). Affinity was measured using BIAcore X instrument (Biacore AB, Uppsala, Sweden). ED-B and nAchR were immobilized on streptavidin (SA) chip (Biacore) by injecting 2,000 RU biotinylated-EDB. VEGF was immobilized on CM5 chip (Biacore) using EDC/NHS. PBS (pH 7.4) was used as a running buffer. Kinetics at different concentrations was measured under a flow rate of 30 µl/min, and affinity was calculated using BIAevaluation software (Biacore AB, Uppsala, Sweden).

Example 7

Figure 11:
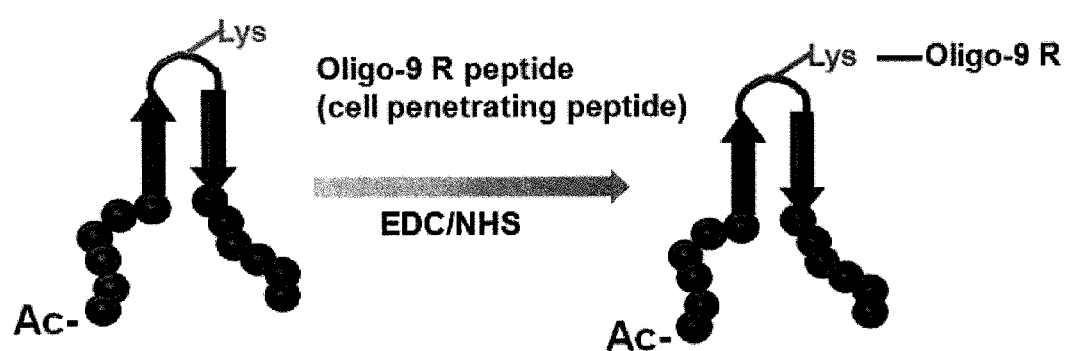
FIG. 11 represents that the bipodal-peptide binder of the present invention plays a specific function in prevention of MyD88 activity in a cell.
Figure 11:
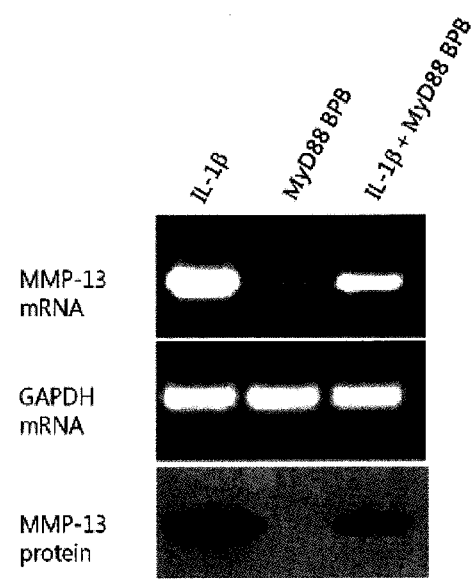

Cancer Targeting of Bipodal-peptide Binder Specific to Fibronectin ED-B as a Cancer Biomarker Cy5.5-NHS fluorescence dye (Amersham Pharmacia, Piscataway) was incubated in 50 mM sodium borate buffer (pH 9.7) at room temperature for 12 hrs with bipodal-peptide binder (peptide 2) which targets fibronectin ED-B widely distributed in cancer cells. After reaction, Cy5.5 and bipodal-peptide binder-Cy5.5 were separated by Sephadex G25 (Pharmacia Biotech, Uppsala, Sweden). Balb/c nude mice (Orient Bio) received subcutaneous injections of $2 \times 10^6$ human U87MG cells (ATCC) and bred for 10 days. Subsequently, mice were intravenously injected with 0.5 nmol bipodal-peptide binder-Cy5.5 and the fluorescence was measured using IVIS (Caliper Life Sience, Hopkinton). This experiment suggests that the bipodal-peptide binder specific to ED-B as a cancer biomarker is accumulated in cancerous tissue of in vivo animal model, demonstrating its application as a practical cancer diagnostics (FIG. 11).

Example 8

Inhibition of Bipodal-Peptide Binder Activity Specific to MyD88 Present in a Cell Since MyD88 is a cellular protein, 9 arginines (Anigen, Korea) as a cell penetrating peptide were covalently linked to a lysine residue in loop of bipodal-peptide binder using EDC/NHS (Sigma) for penetration. As activation of MyD88 induces increase of MMP-13 amount, to investigate the amount of MMP-13 may determine whether activity of MyD88 is or not. The activity of MyD88 was activated by treating IL-1beta (10 ng/ml; R&D systems, Minneapolis, Minn.) to chondrocytes. Next, 10 µM bipodal-peptide binder specific to MyD88 (peptide 1 in Table 3f) was treated to chondrocytes for 12 hrs, and then mRNA was extracted, followed by performing RT-PCR for MMP-13 and GAPDH. In addition, cellular proteins were obtained from chondrocytes and Western blotting was carried out using Anti-MMP13 antibody (Abcam, ab3208, Cambridge) and semi-dry transfer machine (Amersham Bioscience, Piscataway) to determine the amount of MMP-13.
Experiment Results Example 9

Construction of Bipodal-peptide Binder Library

Stable β-hairpin motif was used as a structure stabilizing region of dipodal peptide binder. Given that interactions between tryptophan and tryptophan amino acids contributes to structure stability of β-hairpin motif, tryptophan (Trp) zipper motif was utilized (Andrea et al., Proc. Natl. Acad. Sci. 98:5578-5583(2001)). Each 6 amino acids in N- and C-terminal region of Trp zipper as a backbone were randomly arranged to produce variable region in both terminals (FIG. 1a). It was designated as a bipodal-peptide binder. The bipodal-peptide binder has high affinity and specificity since it binds to antibody in a cooperative manner via variable region in both termini. Additionally, the structure stabilizing region of bipodal-peptide binder may be diversely composed as demonstrated in FIGS. 1b-1e.

Figure 2:
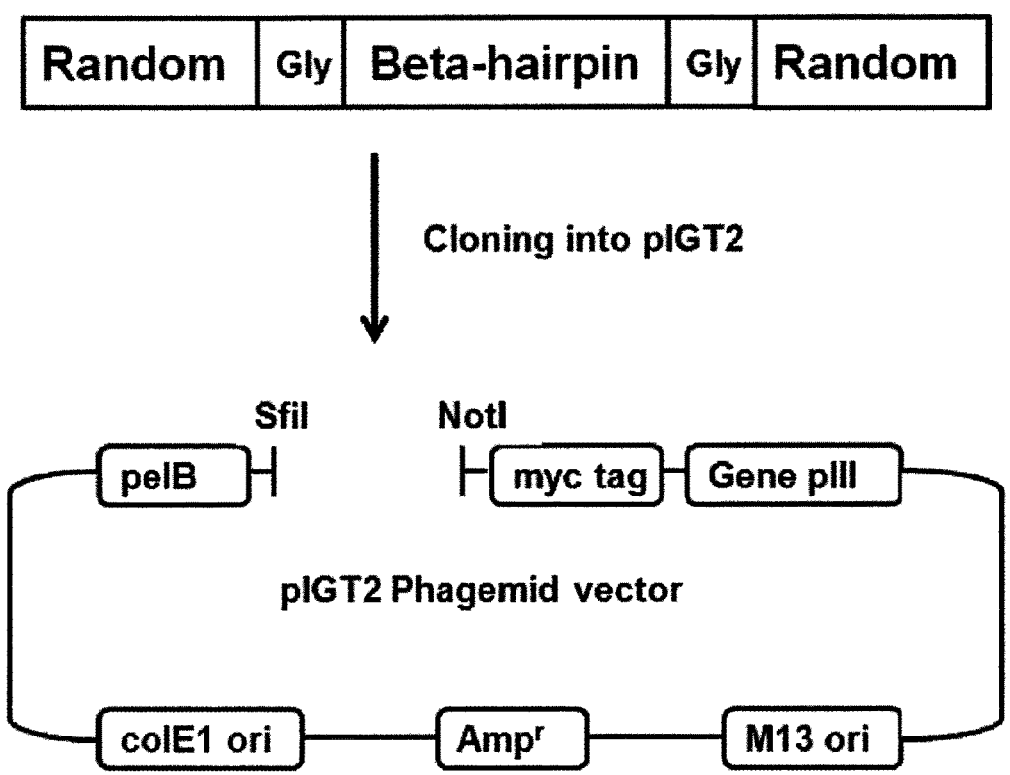
FIG. 2 shows a strategy for cloning a bipodal-peptide binder library. In a map of pIGT2 phagemid vector, a pelB signal sequence and myc tag are tagging sequences to determine whether a gene of interest is suitably expressed on phage surface. lac promoter was used as a promoter.

Double strand DNA was prepared by PCR reaction using two degenerate oligonucleotides and restricted with restriction enzymes, SfiI and NofI. Then, DNA was cloned into pIGT2 phagemid vector, constructing a library of not less than $8 \times 10^8$ (FIG. 2).

Example 10

Biopanning

Biopanning to fibronectin ED-B, VEGF, VCAM1, nAchR or HAS protein was carried out 3-5 times using a bipodal-peptide binder library, and the ratio of output phage to input phage of phage peptides recovered from each biopanning step was determined (Table 1a).

TABLE 1a

| Biopanning to fibronectin ED-B protein. | | | |
|---|---|---|---|
| Panning round (times) | Input phage (pfu) | Output phage (pfu) | calculation |
| 1 | $2.8 \times 10^{11}$ | $1.1 \times 10^7$ | $4.0 \times 10^{-5}$ |
| 2 | $1.6 \times 10^{11}$ | $1.0 \times 10^7$ | $5.1 \times 10^{-5}$ |
| 3 | $1.6 \times 10^{11}$ | $2.1 \times 10^7$ | $1.3 \times 10^{-5}$ |

TABLE 1b

| Biopanning to VEGF protein. | | | |
|---|---|---|---|
| Panning round (times) | Input phage (pfu) | Output phage (pfu) | calculation |
| 1 | $1.0 \times 10^{11}$ | $1.0 \times 10^6$ | $10 \times 10^{-5}$ |
| 2 | $2.8 \times 10^{10}$ | $6.5 \times 10^6$ | $23 \times 10^{-5}$ |
| 3 | $1.9 \times 10^{10}$ | $3.1 \times 10^7$ | $189 \times 10^{-5}$ |
| 4 | $1.3 \times 10^{11}$ | $2.1 \times 10^8$ | $161 \times 10^{-5}$ |
| 5 | $3.5 \times 10^{11}$ | $3.7 \times 10^7$ | $100 \times 10^{-5}$ |

TABLE 1c

| Biopanning to VCAM1 protein. | | | |
|---|---|---|---|
| Panning round (times) | Input phage (pfu) | Output phage (pfu) | calculation |
| 1 | $5.4 \times 10^{10}$ | $1.4 \times 10^6$ | $2.5 \times 10^{-5}$ |
| 2 | $4.1 \times 10^{11}$ | $2.3 \times 10^6$ | $0.5 \times 10^{-5}$ |
| 3 | $1.0 \times 10^{12}$ | $3.4 \times 10^7$ | $3.4 \times 10^{-5}$ |
| 4 | $4.0 \times 10^{12}$ | $1.5 \times 10^8$ | $3.7 \times 10^{-5}$ |
| 5 | $7.9 \times 10^{10}$ | $3.3 \times 10^6$ | $4.1 \times 10^{-5}$ |

TABLE 1d

| Biopanning to nAchR protein. | | | |
|---|---|---|---|
| Panning round (times) | Input phage (pfu) | Output phage (pfu) | calculation |
| 1 | $2.6 \times 10^{12}$ | $9.9 \times 10^7$ | $3.1 \times 10^{-5}$ |
| 2 | $7.9 \times 10^{11}$ | $4.6 \times 10^7$ | $5.8 \times 10^{-5}$ |
| 3 | $2.0 \times 10^{12}$ | $5.6 \times 10^8$ | $28.3 \times 10^{-5}$ |
| 4 | $3.3 \times 10^{12}$ | $3.2 \times 10^9$ | $97.6 \times 10^{-5}$ |
| 5 | $3.3 \times 10^{11}$ | $6.7 \times 10^8$ | $202 \times 10^{-5}$ |

TABLE 1e

| Biopanning to HSA protein. | | | |
|---|---|---|---|
| Panning round (times) | Input phage (pfu) | Output phage (pfu) | calculation |
| 1 | $2.6 \times 10^{11}$ | $1.7 \times 10^7$ | $6.5 \times 10^{-5}$ |
| 2 | $5.5 \times 10^9$ | $5.4 \times 10^6$ | $100 \times 10^{-5}$ |
| 3 | $4.1 \times 10^{10}$ | $3.0 \times 10^7$ | $75 \times 10^{-5}$ |
| 4 | $1.4 \times 10^{10}$ | $5.8 \times 10^7$ | $400 \times 10^{-5}$ |
| 5 | $2.0 \times 10^9$ | $4.0 \times 10^7$ | $1,000 \times 10^{-5}$ |

TABLE 1f

| Biopanning to MyD88 protein. | | | |
|---|---|---|---|
| Panning round (times) | Input phage (pfu) | Output phage (pfu) | calculation |
| 1 | $2.0 \times 10^{11}$ | $2.8 \times 10^7$ | $14 \times 10^{-5}$ |
| 2 | $1.3 \times 10^{11}$ | $1.0 \times 10^7$ | $7.7 \times 10^{-5}$ |
| 3 | $1.1 \times 10^{10}$ | $1.8 \times 10^8$ | $163 \times 10^{-5}$ |
| 4 | $4.0 \times 10^{12}$ | $3.3 \times 10^9$ | $8.2 \times 10^{-5}$ |
| 5 | $7.0 \times 10^{10}$ | $1.8 \times 10^8$ | $257 \times 10^{-5}$ |

Example 11

ELISA of Input Phage to Fibronectin ED-B

Figure 3:
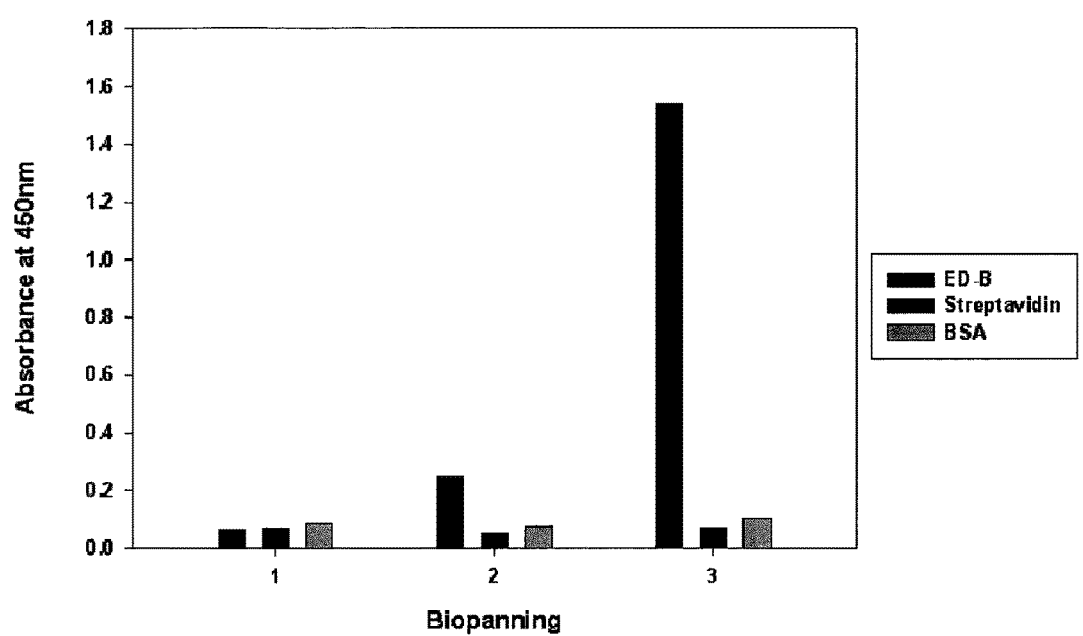
FIG. 3 is a biopanning result of ED-B, streptavidin and BSA to input phage in fibronectin ED-B biopanning process.

ELISA of each input phage of bipodal-peptide binder library was carried out for ED-B, streptavidin and BSA. Binding property of first input phages was similar in all ED-B, streptavidin and BSA, whereas the absorbance of ED-B in second input phage was 5.1-fold and 3.4-fold higher than that of streptavidin and BSA, respectively. The binding property of ED-B in third input phage was 22-fold and 15-fold higher than that of streptavidin and BSA, respectively, suggesting that biopanning to ED-B is successful (FIG. 3 and Table 2).

TABLE 2

| Type | Input phage 1 | Input phage 2 | Input phage 3 |
|---|---|---|---|
| ED-B | 0.062 | 0.249 | 1.544 |
| Streptavidin | 0.070 | 0.048 | 0.068 |
| BSA | 0.088 | 0.073 | 0.102 |

Example 12

Figure 4:
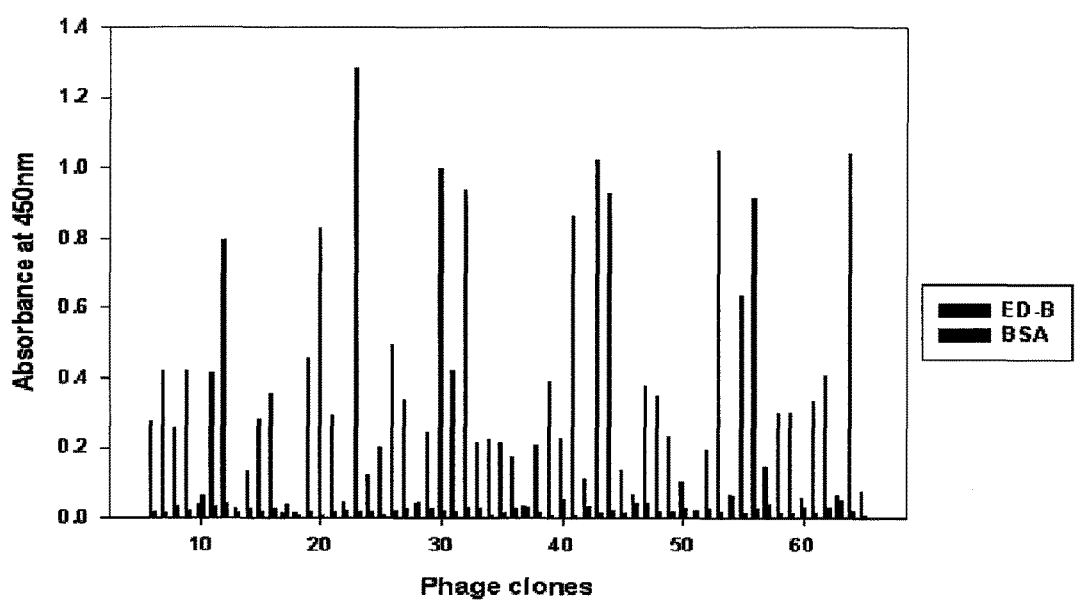
FIG. 4 represents ELISA to ED-B and BSA of 60 recombinant phages recovered from third biopanning of a bipodal-peptide binder library in fibronectin ED-B biopanning process.

Detection of Phage Peptide Specific to Fibronectin ED-B, VEGF, VCAM1, nAchR, HAS and MyD88 protein (Phage ELISA) and Sequencing The phages recovered from biopanning step having the highest ratio of output phage to input phage were isolated as plaques. Sixty plaques were amplified from each plaque, and then ELISA for BSA was carried out (FIG. 4). After selecting clones with higher absorbance compared to BSA, they were sequenced. We isolated peptides specific to each protein which were repetitively found in DNA sequencing (Table 3).

TABLE 3

| Type | Peptide sequence specific to fibronectin ED-B |
|---|---|
| Peptide 1 | MSADKSGSWTWENGKWTWKGQVRTRD (SEQ ID NO: 20) |
| Peptide 2 | HCSSAVGSWTWENGKWTWKGIIRLEQ (SEQ ID NO: 21) |
| Peptide 3 | HSQGSPGSWTWENGKWTWKGRYSHRA (SEQ ID NO: 22) |
| Type | Peptide sequence specific to VEGF |
| Peptide 1 | HANFFQGSWTWENGKWTWKGWKYNQS (SEQ ID NO: 23) |

TABLE 3-continued

| | |
|---|---|
| Peptide 2 | ASPFWAGSWTWENGKWTWKGWVPSNA<br>(SEQ ID NO: 24) |
| Peptide 3 | HAFYYTGSWTWENGKWTWKGWPVTTS<br>(SEQ ID NO: 25) |
| Peptide 4 | YGAYPWGSWTWENGKWTWKGWRVSRD<br>(SEQ ID NO: 26) |
| Peptide 5 | AAPTSFGSWTWENGKWTWKGWQMWHR<br>(SEQ ID NO: 27) |
| Type | Peptide sequence specific to VCAM1 |
| Peptide 1 | QARDCTGSWTWENGKWTWKGPSICPI<br>(SEQ ID NO: 28) |
| Type | Peptide sequence specific to nAchR |
| Peptide 1 | EASFWLGSWTWENGKWTWKGKGTLNR<br>(SEQ ID NO: 29) |
| Peptide 2 | YAYPLLGSWTWENGKWTWKGWYQKWI<br>(SEQ ID NO: 30) |
| Peptide 3 | ASLPAWGSWTWENGKWTWKGWSTRTA<br>(SEQ ID NO: 31) |
| Type | Peptide sequence specific to HSA |
| Peptide 1 | AASPYKGSWTWENGKWTWKGGWRMKM<br>(SEQ ID NO: 32) |
| Peptide 2 | SANSLYGSWTWENGKWTWKGTSRQRW<br>(SEQ ID NO: 33) |
| Peptide 3 | YAHVYYGSWTWENGKWTWKGHRVTQT<br>(SEQ ID NO: 34) |
| Peptide 4 | YGAYPWGSWTWENGKWTWKGWRVSRD<br>(SEQ ID NO: 35) |
| Peptide 5 | YAHFGWGSWTWENGKWTWKGTTDSQS<br>(SEQ ID NO: 36) |
| Type | Peptide sequence specific to MyD88 |
| Peptide 1 | HSHAFYGSWTWENGKWTWKGNPGWWT<br>(SEQ ID NO: 37) |
| Peptide 2 | ASTINFGSWTWENGKWTWKGYTRRWN<br>(SEQ ID NO: 38) |

Example 13

Affinity Measurement to Fibronectin ED-B, VEGF, VCAM1, nAchR and HAS

Figure 5A:
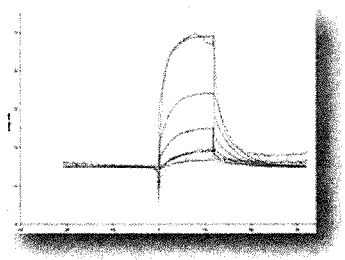
FIG. 5*a* is a result to monitor an affinity of the bipodal-peptide binder of the present invention to be specifically bound to fibronectin ED-B.
Figure 5A:
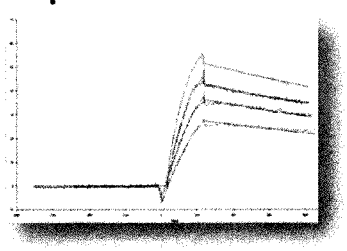
Figure 5A:
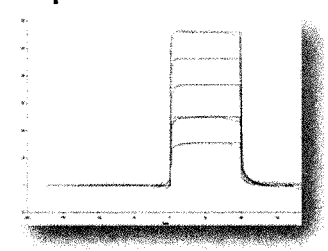
Figure 5B:
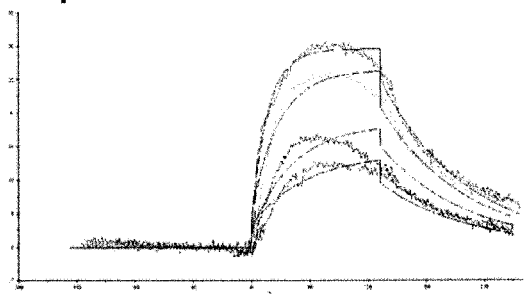
FIG. 5*b* shows a result to monitor an affinity of the bipodal-peptide binder of the present invention to be specifically bound to VEGF.
Figure 5B:
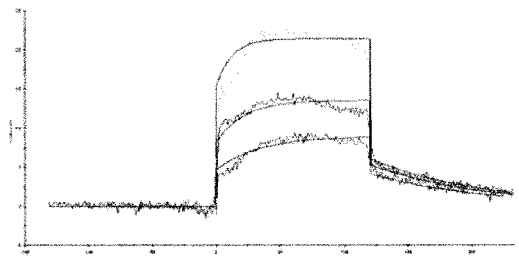
Figure 5C:
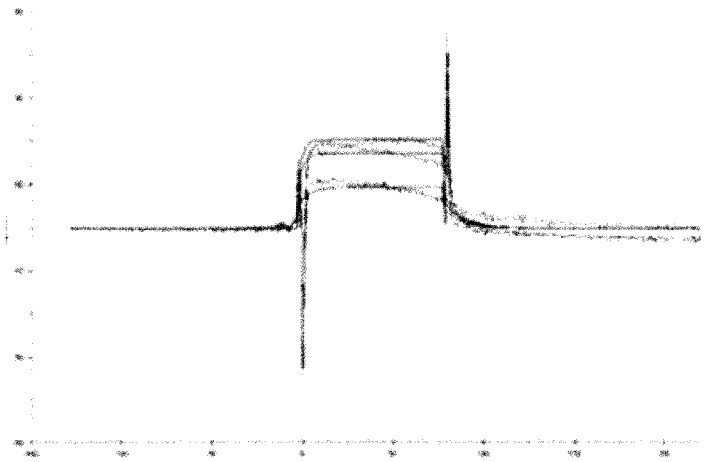
FIG. 5*c* represents a result to monitor an affinity of the bipodal-peptide binder of the present invention to be specifically bound to VCAM1.
Figure 5D:
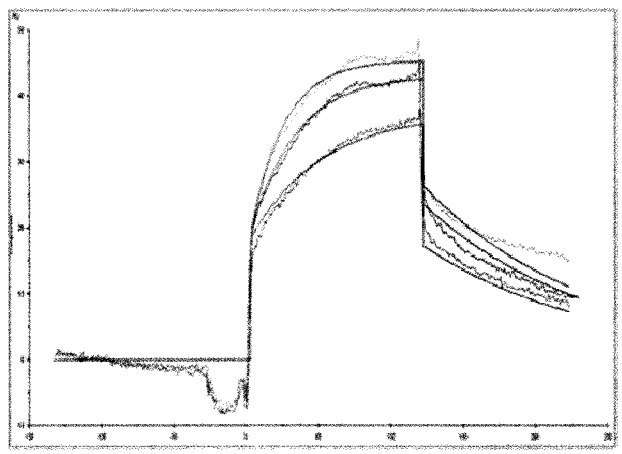
FIG. 5*d* shows a result to monitor an affinity of the bipodal-peptide binder of the present invention to be specifically bound to nAchR (Nicotinic acetylcholine receptor).
Figure 5E:
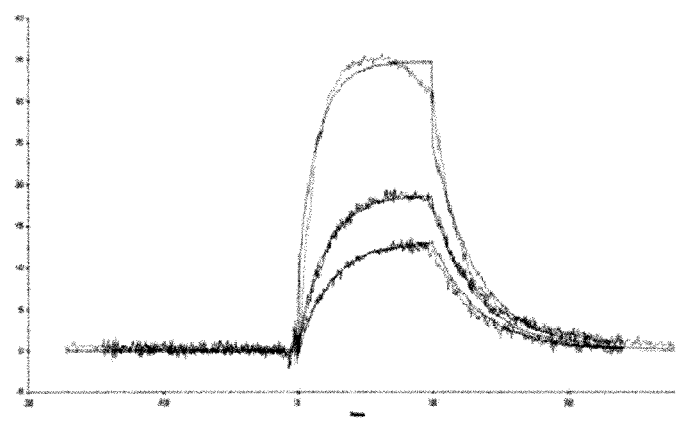
FIG. 5*e* is a result to measure an affinity of the bipodal-peptide binder of the present invention to be specifically bound to HAS (Human Serum Albumin).

The above-mentioned peptides were synthesized and their affinities to fibronectin ED-B, VEGF, VCAM1, nAchR and HAS were measured using SPR Biacore system (Biacore AB, Uppsala, Sweden). In affinity measurement for fibronectin ED-B, each peptide 1, 2 and 3 was 620 nM, 75 nM and 2.5 µM (FIG. 5a). In VEGF, peptide 1 and 2 exhibited an affinity of 60 nM and 326 nM (FIG. 5b), respectively. In peptide fragment for VCAM1, peptide 1 had an affinity of 318 nM (FIG. 5c). In peptide fragment for nAchR, peptide 1 had an affinity of 73 nM (FIG. 5d). Finally, peptide 1 was 115 nM in affinity measurement to peptide fragment for HSA (FIG. 5e).

Example 14

Specificity Analysis to Fibronectin ED-B, VEGF, VCAM1, nAchR and HAS

Figure 6A:
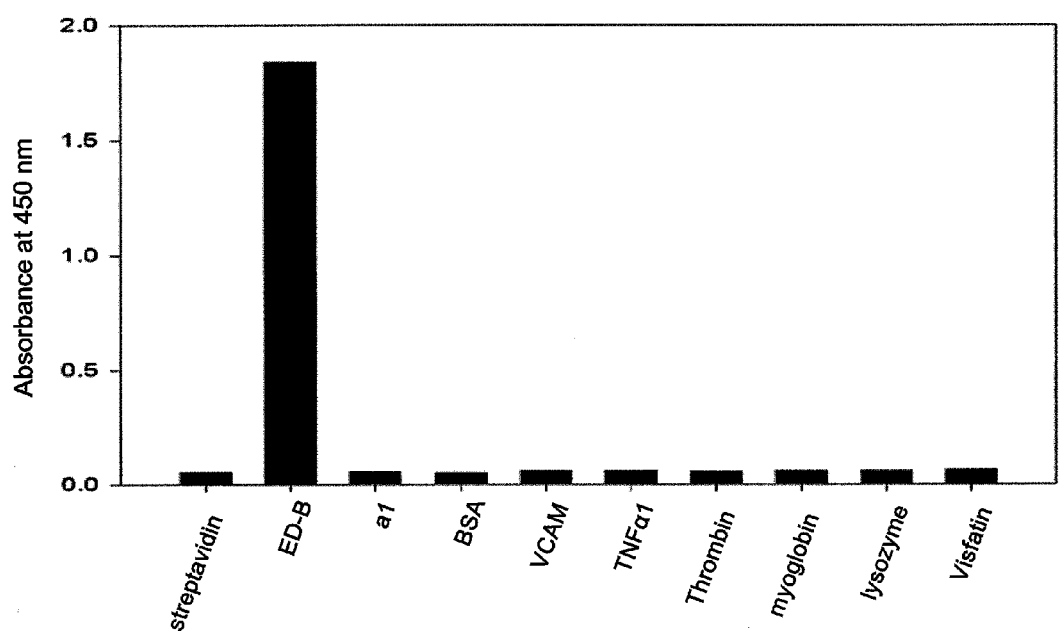
FIG. 6*a* is a graph to measure absorbance through ELISA against several proteins using a recombinant phage containing the bipodal-peptide binder of the present invention to examine specificity to fibronectin ED-B. X axis is in a order of streptavidin, ED-B, acetylcholine α1 (a1), BSA, VCAM, TNF-α, thrombin, myoglobin, lysozyme and visfatin from the left bar.
Figure 6B:
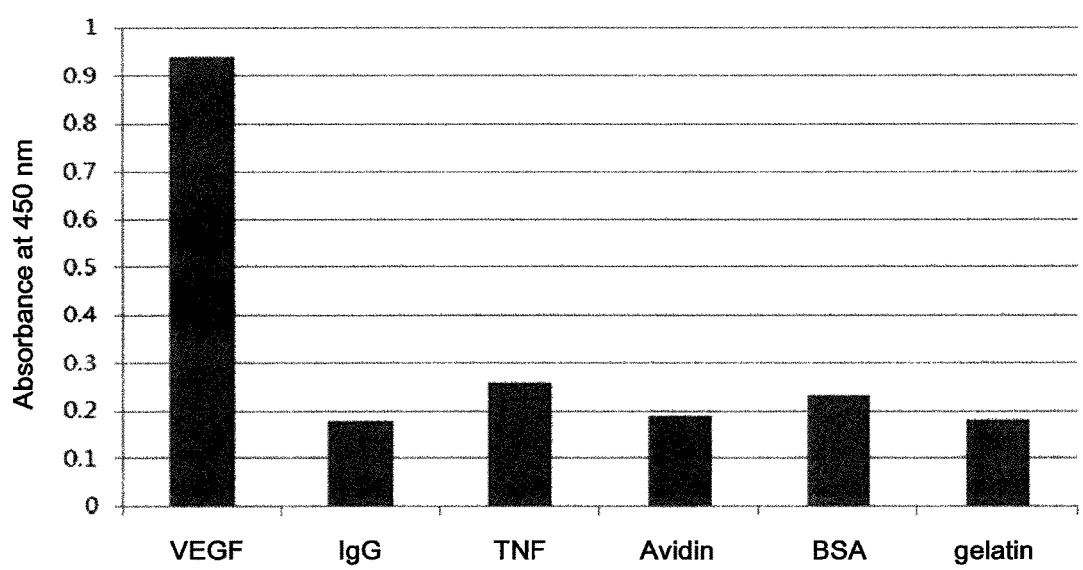
FIG. 6*b* shows a graph to measure absorbance through ELISA against several proteins using a recombinant phage containing the bipodal-peptide binder of the present invention to examine specificity to VEGF.
Figure 6C:
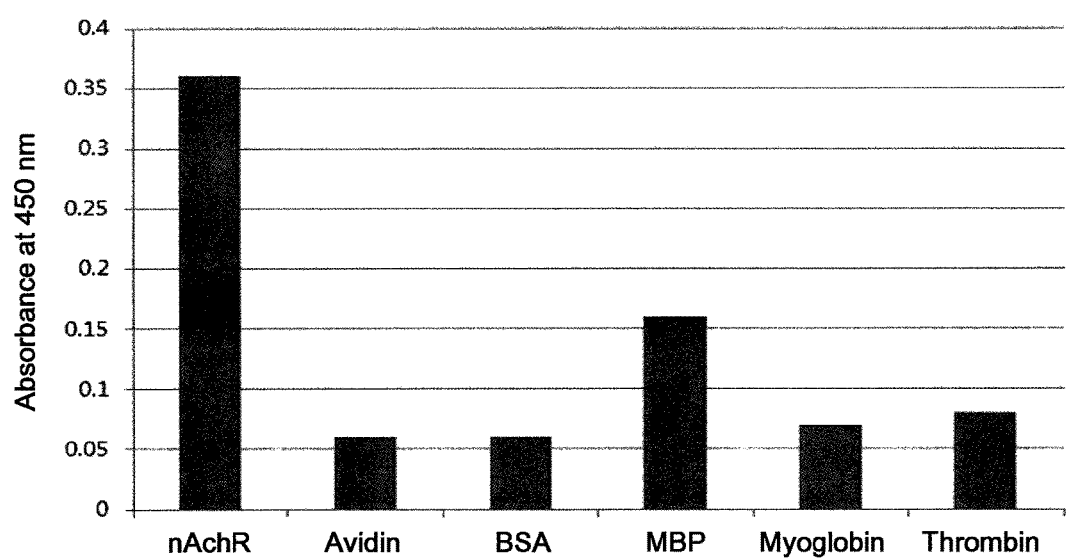
FIG. 6*c* represents a graph to measure absorbance through ELISA against several proteins using a recombinant phage containing the bipodal-peptide binder of the present invention to examine specificity to VCAM1.
Figure 6D:
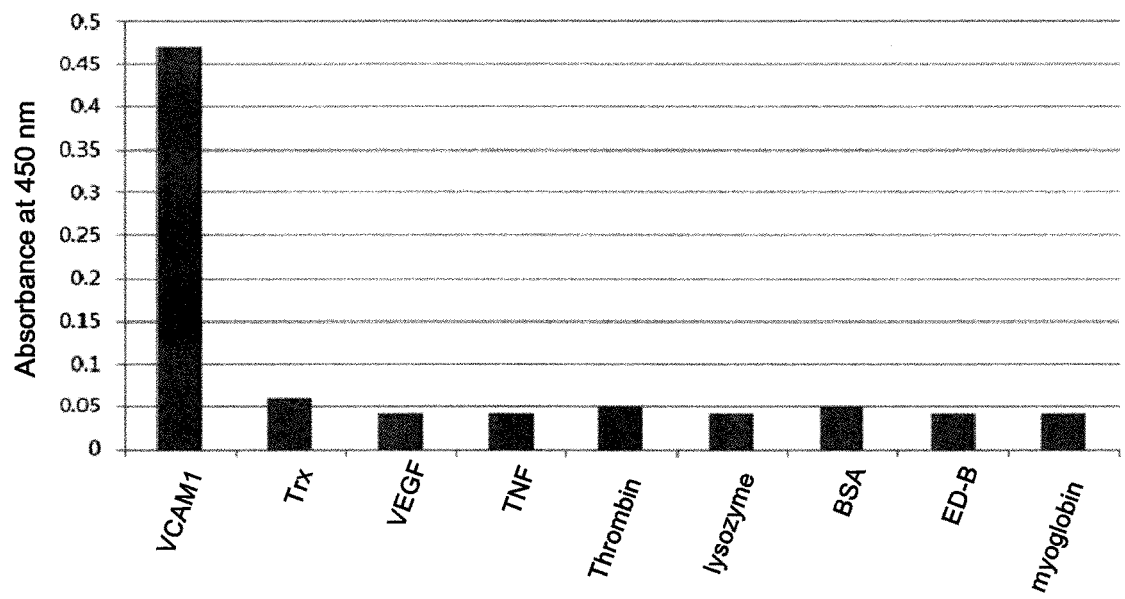
FIG. 6*d* is a graph to measure absorbance through ELISA against several proteins using a recombinant phage containing the bipodal-peptide binder of the present invention to examine specificity to nAchR.
Figure 6E:
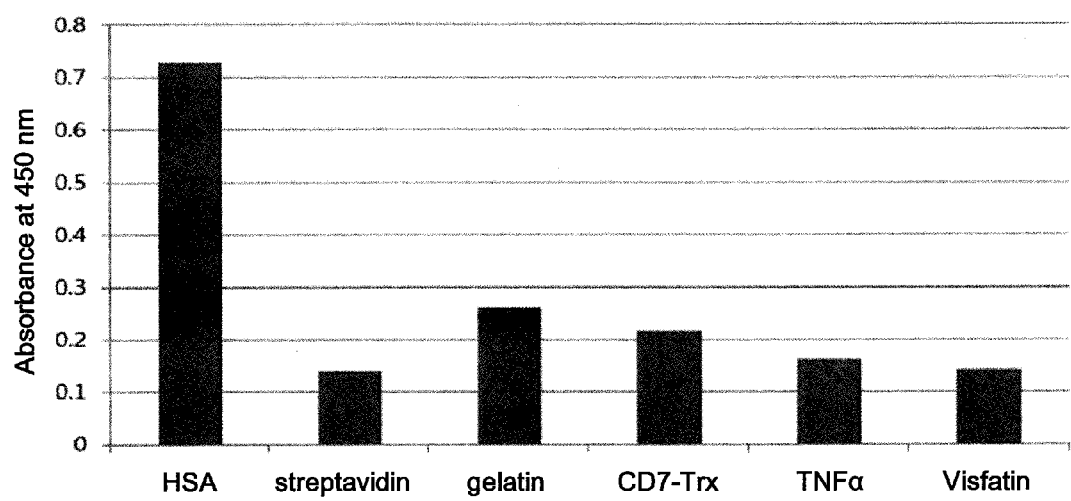
FIG. 6*e* represents a graph to measure absorbance through ELISA against several proteins using a recombinant phage containing the bipodal-peptide binder of the present invention to examine specificity to HSA.
Figure 6F:
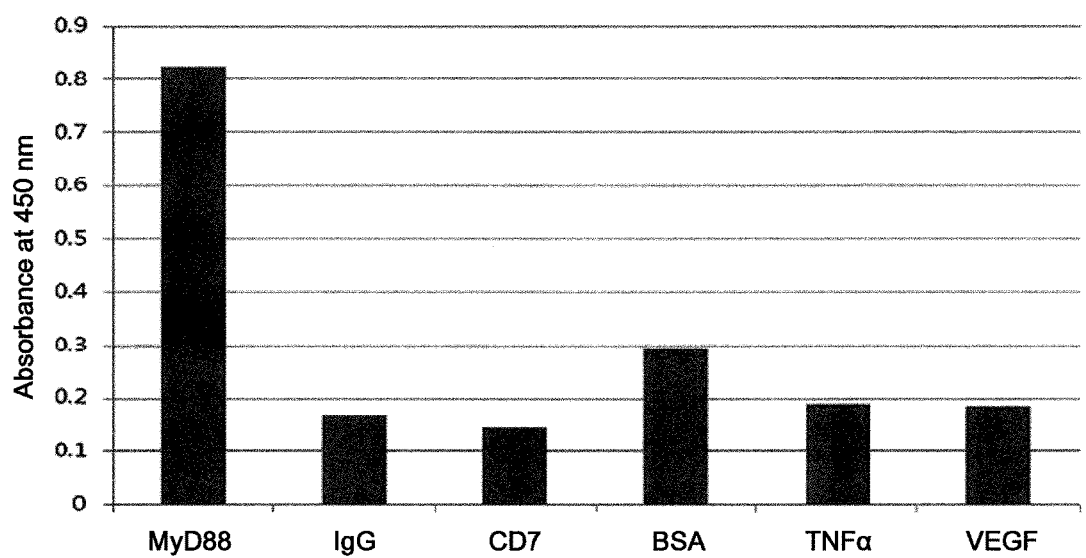
FIG. 6*f* shows a graph to measure absorbance through ELISA against several proteins using a recombinant phage containing the bipodal-peptide binder of the present invention to examine specificity to MyD88.

Specificity of recombinant phages to each protein was carried out using ELISA. Each protein (5 µg/ml) was seeded into wells (50 µl per well) in a 96-well ELISA plate and next day, all wells were washed with 0.1% PBST (Tween-20) three times, and blocked at room temperature for 2 hrs using 2% skim milk. Then, the solution was completely removed and the plate was washed with 0.1% PBST three times. Recombinant phages containing the peptide of the present invention were thoroughly mixed with 2% BSA. Each mixture (100 µl) was divided into wells coated with 10 proteins and kept to stand at 27° C. for 2 hrs. After washing with 0.1% PBST 5 times, HRP-conjugated anti-M13 antibodies (1:1,000 dilution; GE Healthcare) were added to each well and incubated at 27° C. for 1 hr. After washing with 0.1% PBST 5 times, 100 µl TMB was divided into each well to induce colorimetric reaction, followed by stopping the reaction adding 100 µl of 1 M HCl. The absorbance was measured at 450 nm. As shown in FIG. 6a, the absorbance of peptide 2 (Table 3a) specific to ED-B isolated from bipodal-peptide binder was measured above 30-fold higher than that of other proteins, suggesting that peptide 2 sequence is specific to ED-B. As shown in FIGS. 6b-6f, it could be appreciated that each peptide 1 in Table 3b-3f has specificity for VEGF, VCAM1, nAchR, HSA and MyD88.

Example 15

Cooperative Effect of SPR (Surface Plasmon Resonance)

Figure 7:
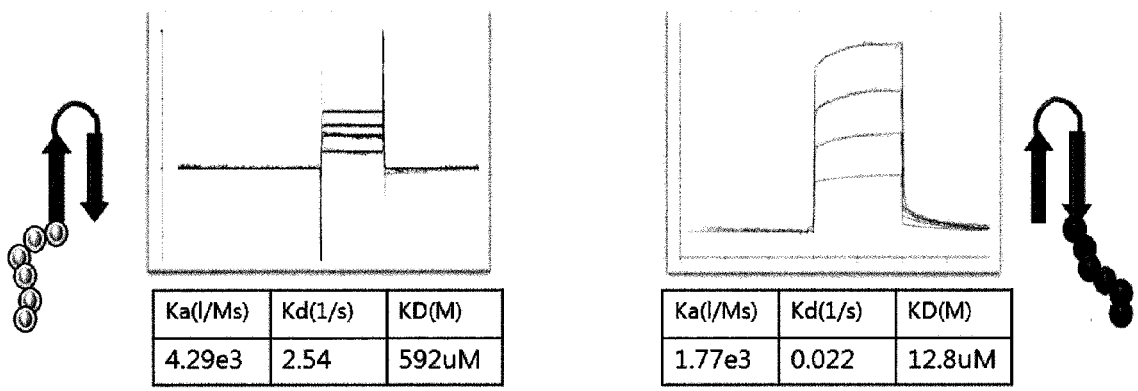
FIG. 7 is a result to monitor an affinity for verifying a cooperative binding activity of the bipodal-peptide binder of the present invention.

To verify cooperative effect of bipodal-peptide binder to antigen, we synthesized two peptides removing either N- or C-terminal region of peptide 2 to ED-B having excellent specificity in Table 3a for affinity measurement. Affinity of N-terminal region and C-terminal region was measured at 592 µM and 12.8 µM, respectively (FIG. 7). It was demonstrated that cooperative effect is generated by bipodal structure necessary in bipodal-peptide binder, and measured at an affinity of 43 nM (FIG. 5a).

Example 16

Binding Assay to Other β-Hairpin

Figure 8:
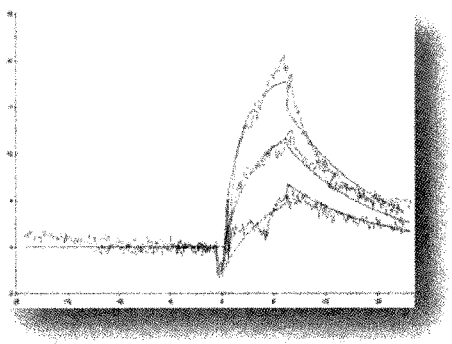
FIG. 8 shows a result to monitor an affinity of the bipodal-peptide binder of the present invention by replacing tryptophan zipper motif with several β-hairpin motifs as a structure stabilizing region in the bipodal-peptide binder.
Figure 8:
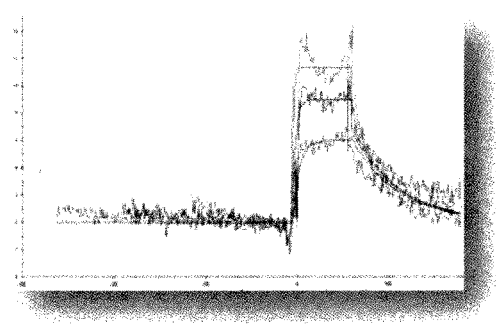

In addition to tryptophan zipper, GB1m3 and HP7 peptide as a type of other β-hairpin backbones were synthesized to contain N-terminal sequence (HCSSAV) and C-terminal sequence (IIRLEQ) of peptide 2 which is specifically bound to ED-B (Anigen, Korea). In other words, the sequence of bipodal-peptide binder in tryptophan zipper is HCSSAVG-SWTWENGKWTWKGIIRLEQ (SEQ ID NO:21), and in GB1m3 and HP7 are HCSSAVGKKWTYNPATGKFT-VQEGIIRLEQ (SEQ ID NO:63) and HCSSAVGKTWN-PATGKWTEGIIRLEQ (SEQ ID NO:64), respectively. Affinity of each peptide was measured using BIAcore X (Biacore AB, Uppsala, Sweden). ED-B was immobilized on streptavidin (SA) chip (Biacore) by injecting 2,000 RU biotinylated-EDB. PBS (pH 7.4) was used as a running buffer. Kinetics at different concentrations was measured under a flow rate of 30 µl/min, and affinity was calculated using BIAevaluation software. As a result, affinity of each GB1m3 and HP7 was 70 nM and 84 nM, demonstrating that affinities of both GB1m3 and HP7 are similar to that of tryptophan zipper (43 nM) (FIG. 8). It could be appreciated that all stable β-hairpin motifs may function as a structure stabilizing region.

Example 17

Figure 9:
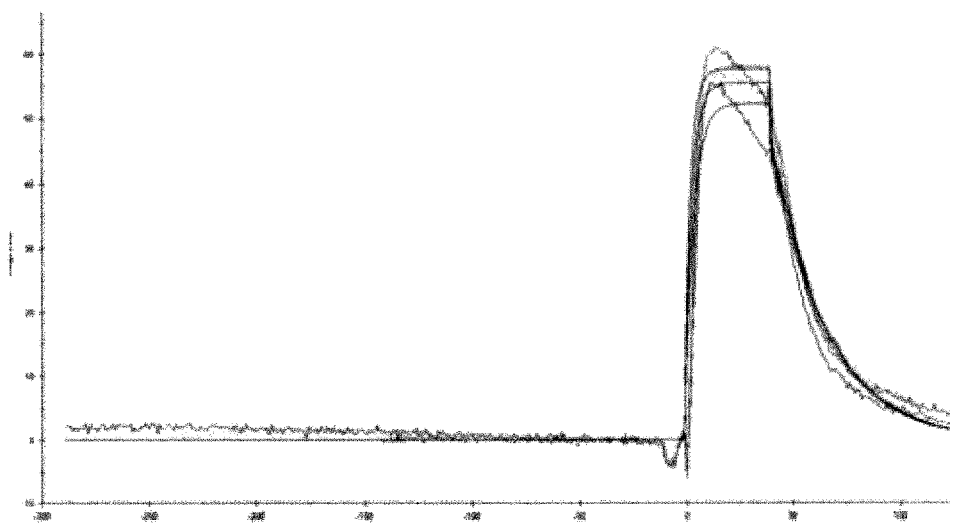
FIG. 9 represents a result to monitor an affinity of the bipodal-peptide binder of the present invention by replacing tryptophan zipper motif with a leucine zipper motif as a structure stabilizing region in the bipodal-peptide binder.

Binding Assay to Bipodal-peptide Binder Containing Leucine Zipper as a Structure Stabilizing Region A leucine zipper motif as a structure stabilizing region instead of β-hairpin structure was synthesized to contain N-terminal sequence (HCSSAV) and C-terminal sequence (IIRLEQ) of peptide 2 which is specifically bound to ED-B, producing two peptides, CSSPIQGGSMKQLEDKVEELL-SKNYHLENEVARLKKLVGER (SEQ ID NO:40) and IIRLEQGGSMKQLEDKVEELLSKNYHLENEVARLK-KLVGER (SEQ ID NO:41) (Anigen, Korea). Both peptides were formed as dimer, and their affinities were measured using BIAcore X (Biacore AB, Uppsala, Sweden). As a result, affinity of leucine zipper was 5 μM, demonstrating that affinities of leucine zipper are lower than that of tryptophan zipper (43 nM). However, it may be possible to utilize a leucine zipper as a structure stabilizing region in bipodal-peptide binder (FIG. 9).

Example 18

Figure 10:
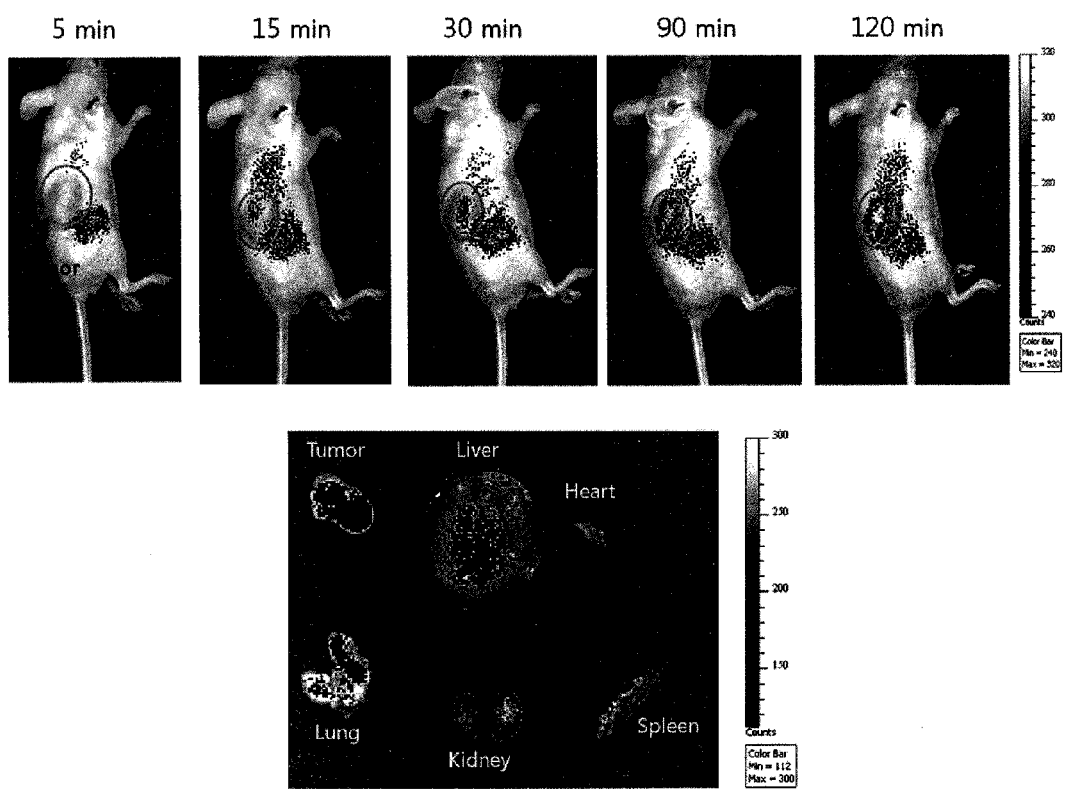
FIG. 10 represents a cancer targeting of the bipodal-peptide binder of the present invention specific to fibronectin ED-B as a cancer biomarker. It was shown that the bipodal-peptide binder is accumulated in a tumor portion of mouse with the passage of time. In addition, it was observed that the bipodal-peptide binder is significantly accumulated in each internal organ (e.g., liver, heart, lung, kidney, spleen, etc.) through fluorescence measurement.

Cancer Targeting of Bipodal-peptide Binder Specific to Fibronectin ED-B as a Cancer Biomarker After Cy5.5-NHS fluorescence dye was linked to bipodal-peptide binder which targets fibronectin ED-B widely distributed in cancer cells, mice injected with human U87MG cells were intravenously administered with bipodal-peptide binder-Cy5.5, followed by measuring fluorescence through IVIS to determine whether the bipodal-peptide binder may target cancerous tissue (FIG. 10). As a result, it was shown that the bipodal-peptide binder specific to fibronectin ED-B as a cancer biomarker was accumulated in cancer tissue, suggesting that the bipodal-peptide binder of the present invention may be efficiently utilized in in vivo imaging.

Example 19

Inhibition of Bipodal-peptide Binder Activity Specific to MyD88 Present in a Cell It was demonstrated that bipodal-peptide binder had specific effect on preventing an activity of cellular MyD88 (FIG. 11). Bipodal-peptide binder was attached with a cell penetrating peptide for penetration. After treating IL-1beta, chondrocytes were incubated with 10 μM bipodal-peptide binder specific to MyD88, resulting in inhibition of MyD88 activity. It was confirmed via reduction of MMP-13 mRNA and protein level. These results suggest that bipodal-peptide binder may inhibit an activity of cellular target.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A bipodal peptide binder which specifically binds to a target, comprising:
   (a) a tryptophan zipper motif as a structure stabilizing region; and
   (b) a target binding region I linked to one terminus of the tryptophan zipper motif and a target binding region II linked to the other terminus of the tryptophan zipper motif, wherein the target binding region I and the target binding region II are covalently linked through the structure stabilizing region and are each a peptide that has binding affinity for the target, and wherein the number of amino acid residues of each of target binding region I and target binding region II is an integer of 2-50,
   wherein the amino acid sequence of said bipodal peptide binder is non-naturally occurring.

2. The bipodal peptide binder according to claim 1, wherein the tryptophan zipper motif comprises an amino acid sequence selected from the group consisting of SEQ ID NOs: 1-3 and 5-10.

3. The bipodal peptide binder according to claim 1, wherein the tryptophan zipper motif is represented by the following Formula I:

$$X_1\text{-Trp}(X_2)X_3\text{-}X_4\text{-}X_5(X'_2)X_6\text{-}X_7 \qquad \text{Formula I}$$

wherein $X_1$ represents Ser or Gly-Glu, and $X_2$ and $X'_2$ independently represent Thr, His, Val, Ile, Phe or Tyr, and $X_3$ represents Trp or Tyr, and $X_4$ represents type I, type I', type II, type II', type III or type III' turn sequence, and $X_5$ represents Trp or Phe, and $X_6$ represents Trp or Val, and $X_7$ represents Lys or Thr-Glu.

4. The bipodal peptide binder according to claim 3, wherein the tryptophan zipper motif is represented by the Formula I in which $X_1$ represents Ser or Gly-Glu, and $X_2$ and $X'_2$ independently represent Thr, His or Val, and $X_3$ represents Trp or Tyr, and $X_4$ represents type I, type I', type II or type II' turn sequence, and $X_5$ represents Trp or Phe, and $X_6$ represents Trp or Val, and $X_7$ represents Lys or Thr-Glu.

5. The bipodal peptide binder according to claim 1, wherein the number of amino acid residues of each of the target binding region I and the target binding region II is an integer of 2-20.

6. The bipodal peptide binder according to claim 1, wherein the target binding region I and the target binding region II bind in a cooperative manner to the target.

7. The bipodal peptide binder according to claim 1, wherein the structure stabilizing region, the target binding region I or the target binding region II further comprises a functional molecule.

8. The bipodal peptide binder according to claim 7, wherein the functional molecule comprises a label capable of generating a detectable signal, a chemical drug, a biodrug, a cell penetrating peptide (CPP) or a nanoparticle.

9. The bipodal peptide binder according to claim 1, wherein the target comprises a biochemical material, a peptide, a polypeptide, a nucleic acid, a carbohydrate, a lipid, a cell, a tissue, a compound, a metal material or a non-metal material.

10. The bipodal peptide binder according to claim 1, wherein the number of amino acid residues of each of the target binding region I and the target binding region II is an integer of 3-10.

* * * * *

```
SEQUENCE LISTING

<160> NUMBER OF SEQ ID NOS: 64

<210> SEQ ID NO 1
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(12)
<223> OTHER INFORMATION: Trpzip1

<400> SEQUENCE: 1

Ser Trp Thr Trp Glu Gly Asn Lys Trp Thr Trp Lys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(12)
<223> OTHER INFORMATION: Trpzip2

<400> SEQUENCE: 2

Ser Trp Thr Trp Glu Asn Gly Lys Trp Thr Trp Lys
1               5                   10
```

```
<210> SEQ ID NO 3
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(12)
<223> OTHER INFORMATION: Trpzip3

<400> SEQUENCE: 3

Ser Trp Thr Trp Glu Pro Asn Lys Trp Thr Trp Lys
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(16)
<223> OTHER INFORMATION: gb1, 41-56

<400> SEQUENCE: 4

Gly Glu Trp Thr Tyr Asp Asp Ala Thr Lys Thr Phe Thr Val Thr Glu
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(16)
<223> OTHER INFORMATION: Trpzip4

<400> SEQUENCE: 5

Gly Glu Trp Thr Trp Asp Asp Ala Thr Lys Thr Trp Thr Trp Thr Glu
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(16)
<223> OTHER INFORMATION: Trpzip5

<400> SEQUENCE: 6

Gly Glu Trp Thr Tyr Asp Asp Ala Thr Lys Thr Phe Thr Trp Thr Glu
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(16)
<223> OTHER INFORMATION: Trpzip6
```

```
<400> SEQUENCE: 7

Gly Glu Trp Thr Trp Asp Asp Ala Thr Lys Thr Trp Thr Val Thr Glu
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(16)
<223> OTHER INFORMATION: Trpzip7

<400> SEQUENCE: 8

Gly Glu Trp His Trp Asp Asp Ala Thr Lys Thr Trp Val Trp Thr Glu
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(16)
<223> OTHER INFORMATION: Trpzip8

<400> SEQUENCE: 9

Gly Glu Trp Val Trp Asp Asp Ala Thr Lys Thr Trp His Trp Thr Glu
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(16)
<223> OTHER INFORMATION: Trpzip9

<400> SEQUENCE: 10

Gly Glu Trp Val Trp Asp Asp Ala Thr Lys Thr Trp Val Trp Thr Glu
1               5                   10                  15

<210> SEQ ID NO 11
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(12)
<223> OTHER INFORMATION: (T3V)-HP6

<400> SEQUENCE: 11

Lys Tyr Val Trp Ser Asn Gly Lys Trp Thr Val Glu
1               5                   10

<210> SEQ ID NO 12
<211> LENGTH: 12
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MISC_FEATURE
<222> LOCATION: (1)..(12)
<223> OTHER INFORMATION: Espinosa-GB1(b)

<400> SEQUENCE: 12

Arg Trp Gln Tyr Val Asn Gly Lys Phe Thr Val Gln
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(16)
<223> OTHER INFORMATION: GB1m2

<400> SEQUENCE: 13

Gly Glu Trp Thr Tyr Asn Pro Ala Thr Gly Lys Phe Thr Val Thr Glu
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(16)
<223> OTHER INFORMATION: GB1m3

<400> SEQUENCE: 14

Lys Lys Trp Thr Tyr Asn Pro Ala Thr Gly Lys Phe Thr Val Gln Glu
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(16)
<223> OTHER INFORMATION: HP5W4

<400> SEQUENCE: 15

Lys Lys Trp Thr Tyr Asn Pro Ala Thr Gly Lys Trp Thr Trp Gln Glu
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(16)
<223> OTHER INFORMATION: HP5W

<400> SEQUENCE: 16

Lys Lys Tyr Thr Trp Asn Pro Ala Thr Gly Lys Trp Thr Val Gln Glu
1               5                   10                  15
```

<210> SEQ ID NO 17
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(16)
<223> OTHER INFORMATION: HP5A

<400> SEQUENCE: 17

Lys Lys Tyr Thr Trp Asn Pro Ala Thr Gly Lys Ala Thr Val Gln Glu
1               5                   10                  15

<210> SEQ ID NO 18
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(12)
<223> OTHER INFORMATION: HP7

<400> SEQUENCE: 18

Lys Thr Trp Asn Pro Ala Thr Gly Lys Trp Thr Glu
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(10)
<223> OTHER INFORMATION: Chignolin

<400> SEQUENCE: 19

Gly Tyr Asp Pro Glu Thr Gly Thr Trp Gly
1               5                   10

<210> SEQ ID NO 20
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-EB-B1

<400> SEQUENCE: 20

Met Ser Ala Asp Lys Ser Gly Ser Trp Thr Trp Glu Asn Gly Lys Trp
1               5                   10                  15

Thr Trp Lys Gly Gln Val Arg Thr Arg Asp
            20                  25

<210> SEQ ID NO 21
<211> LENGTH: 26
<212> TYPE: PRT
<213> ORGANISM: Artificial Sequence
<220> FEATURE:
<223> OTHER INFORMATION: Synthetic Construct
<220> FEATURE:

```
<221> NAME/KEY: MISC_FEATURE
<222> LOCATION: (1)..(26)
<223> OTHER INFORMATION: BPB-ED-B2

<400> SEQUENCE: 21

His Cys Ser Ser Ala Val Gly Ser Trp Thr Trp Glu Asn Gly Lys Trp
1               5                   10                  15

Thr Trp Lys Gly Ile Ile Arg Leu Glu Gln
            20                  25

<210> SEQ ID NO 22
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-ED-B3

<400> SEQUENCE: 22

His Ser Gln Gly Ser Pro Gly Ser Trp Thr Trp Glu Asn Gly Lys Trp
1               5                   10                  15

Thr Trp Lys Gly Arg Tyr Ser His Arg Ala
            20                  25

<210> SEQ ID NO 23
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-VEGF1

<400> SEQUENCE: 23

His Ala Asn Phe Phe Gln Gly Ser Trp Thr Trp Glu Asn Gly Lys Trp
1               5                   10                  15

Thr Trp Lys Gly Trp Lys Tyr Asn Gln Ser
            20                  25

<210> SEQ ID NO 24
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-VEGF2

<400> SEQUENCE: 24

Ala Ser Pro Phe Trp Ala Gly Ser Trp Thr Trp Glu Asn Gly Lys Trp
1               5                   10                  15

Thr Trp Lys Gly Trp Val Pro Ser Asn Ala
            20                  25

<210> SEQ ID NO 25
<211> LENGTH: 26
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (1)..(26)
<223> OTHER INFORMATION: BPB-VEGF3

<400> SEQUENCE: 25

His Ala Phe Tyr Tyr Thr Gly Ser Trp Thr Trp Glu Asn Gly Lys Trp
1               5                   10                  15

Thr Trp Lys Gly Trp Pro Val Thr Thr Ser
            20                  25

<210> SEQ ID NO 26
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-VEGF4

<400> SEQUENCE: 26

Tyr Gly Ala Tyr Pro Trp Gly Ser Trp Thr Trp Glu Asn Gly Lys Trp
1               5                   10                  15

Thr Trp Lys Gly Trp Arg Val Ser Arg Asp
            20                  25

<210> SEQ ID NO 27
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-VEGF5

<400> SEQUENCE: 27

Ala Ala Pro Thr Ser Phe Gly Ser Trp Thr Trp Glu Asn Gly Lys Trp
1               5                   10                  15

Thr Trp Lys Gly Trp Gln Met Trp His Arg
            20                  25

<210> SEQ ID NO 28
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-VCAM1

<400> SEQUENCE: 28

Gln Ala Arg Asp Cys Thr Gly Ser Trp Thr Trp Glu Asn Gly Lys Trp
1               5                   10                  15

Thr Trp Lys Gly Pro Ser Ile Cys Pro Ile
            20                  25

<210> SEQ ID NO 29
<211> LENGTH: 26
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-nAchR1

<400> SEQUENCE: 29

Glu Ala Ser Phe Trp Leu Gly Ser Trp Thr Trp Glu Asn Gly Lys Trp
1               5                   10                  15

Thr Trp Lys Gly Lys Gly Thr Leu Asn Arg
            20                  25

<210> SEQ ID NO 30
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-nAchR2

<400> SEQUENCE: 30

Tyr Ala Tyr Pro Leu Leu Gly Ser Trp Thr Trp Glu Asn Gly Lys Trp
1               5                   10                  15

Thr Trp Lys Gly Trp Tyr Gln Lys Trp Ile
            20                  25

<210> SEQ ID NO 31
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-nAchR3

<400> SEQUENCE: 31

Ala Ser Leu Pro Ala Trp Gly Ser Trp Thr Trp Glu Asn Gly Lys Trp
1               5                   10                  15

Thr Trp Lys Gly Trp Ser Thr Arg Thr Ala
            20                  25

<210> SEQ ID NO 32
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-BSA1

<400> SEQUENCE: 32

Ala Ala Ser Pro Tyr Lys Gly Ser Trp Thr Trp Glu Asn Gly Lys Trp
1               5                   10                  15

Thr Trp Lys Gly Gly Trp Arg Met Lys Met
            20                  25

<210> SEQ ID NO 33
<211> LENGTH: 26
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-BSA2

<400> SEQUENCE: 33

Ser Ala Asn Ser Leu Tyr Gly Ser Trp Thr Trp Glu Asn Gly Lys Trp
1               5                   10                  15

Thr Trp Lys Gly Thr Ser Arg Gln Arg Trp
            20                  25

<210> SEQ ID NO 34
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-BSA3

<400> SEQUENCE: 34

Tyr Ala His Val Tyr Tyr Gly Ser Trp Thr Trp Glu Asn Gly Lys Trp
1               5                   10                  15

Thr Trp Lys Gly His Arg Val Thr Gln Thr
            20                  25

<210> SEQ ID NO 35
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-BSA4

<400> SEQUENCE: 35

Tyr Gly Ala Tyr Pro Trp Gly Ser Trp Thr Trp Glu Asn Gly Lys Trp
1               5                   10                  15

Thr Trp Lys Gly Trp Arg Val Ser Arg Asp
            20                  25

<210> SEQ ID NO 36
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-BSA5

<400> SEQUENCE: 36

Tyr Ala His Phe Gly Trp Gly Ser Trp Thr Trp Glu Asn Gly Lys Trp
1               5                   10                  15

Thr Trp Lys Gly Thr Thr Asp Ser Gln Ser
            20                  25

<210> SEQ ID NO 37
<211> LENGTH: 26
<212> TYPE: PRT
```

<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-MyD88-1

<400> SEQUENCE: 37

His Ser His Ala Phe Tyr Gly Ser Trp Thr Trp Glu Asn Gly Lys Trp
1               5                   10                  15

Thr Trp Lys Gly Asn Pro Gly Trp Trp Thr
            20                  25

<210> SEQ ID NO 38
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: BPB-MyD88-2

<400> SEQUENCE: 38

Ala Ser Thr Ile Asn Phe Gly Ser Trp Thr Trp Glu Asn Gly Lys Trp
1               5                   10                  15

Thr Trp Lys Gly Tyr Thr Arg Arg Trp Asn
            20                  25

<210> SEQ ID NO 39
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(35)
<223> OTHER INFORMATION: Leucine zipper for BPB

<400> SEQUENCE: 39

Gly Gly Ser Met Lys Gln Leu Glu Asp Lys Val Glu Glu Leu Leu Ser
1               5                   10                  15

Lys Asn Tyr His Leu Glu Asn Glu Val Ala Arg Leu Lys Lys Leu Val
            20                  25                  30

Gly Glu Arg
        35

<210> SEQ ID NO 40
<211> LENGTH: 41
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(41)
<223> OTHER INFORMATION: BPBLeu-ED-B-1

<400> SEQUENCE: 40

Cys Ser Ser Pro Ile Gln Gly Gly Ser Met Lys Gln Leu Glu Asp Lys
1               5                   10                  15

Val Glu Glu Leu Leu Ser Lys Asn Tyr His Leu Glu Asn Glu Val Ala
            20                  25                  30

Arg Leu Lys Lys Leu Val Gly Glu Arg
        35                  40

<210> SEQ ID NO 41
<211> LENGTH: 41
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(41)
<223> OTHER INFORMATION: BPBLeu-ED-B-2

<400> SEQUENCE: 41

Ile Ile Arg Leu Glu Gln Gly Gly Ser Met Lys Gln Leu Glu Asp Lys
1               5                   10                  15

Val Glu Glu Leu Leu Ser Lys Asn Tyr His Leu Glu Asn Glu Val Ala
            20                  25                  30

Arg Leu Lys Lys Leu Val Gly Glu Arg
        35                  40

<210> SEQ ID NO 42
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: turn sequence
<220> FEATURE:
<221> NAME/KEY: MOD_RES
<222> LOCATION: (1)..(1)
<223> OTHER INFORMATION: Xaa represents any amino acid selected from 20
      amino acids

<400> SEQUENCE: 42

Xaa Pro Gly Glu Val
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: turn sequence
<220> FEATURE:
<221> NAME/KEY: MOD_RES
<222> LOCATION: (2)..(2)
<223> OTHER INFORMATION: Xaa represents any amino acid selected from 20
      amino acids

<400> SEQUENCE: 43

Ala Xaa Gly Glu Val
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: type I turn sequence

<400> SEQUENCE: 44

Asp Asp Ala Thr Lys Thr
1               5

<210> SEQ ID NO 45
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(4)
<223> OTHER INFORMATION: type I' turn sequence

<400> SEQUENCE: 45

Glu Asn Gly Lys
1

<210> SEQ ID NO 46
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(4)
<223> OTHER INFORMATION: type II' turn sequence

<400> SEQUENCE: 46

Glu Gly Asn Lys
1

<210> SEQ ID NO 47
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(4)
<223> OTHER INFORMATION: type II' turn sequence

<400> SEQUENCE: 47

Glu Pro Asn Lys
1

<210> SEQ ID NO 48
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(11)
<223> OTHER INFORMATION: tryptophan zipper represented by Formula I
<220> FEATURE:
<221> NAME/KEY: MOD_RES
<222> LOCATION: (1)..(1)
<223> OTHER INFORMATION: Xaa(1) is Ser or Gly
<220> FEATURE:
<221> NAME/KEY: MOD_RES
<222> LOCATION: (2)..(2)
<223> OTHER INFORMATION: Xaa(2) is absent or is Glu when Xaa(1) is Gly
<220> FEATURE:

```
<221> NAME/KEY: MOD_RES
<222> LOCATION: (4)..(4)
<223> OTHER INFORMATION: Xaa(4) is Thr, His, Val, Ile, Phe, or Tyr
<220> FEATURE:
<221> NAME/KEY: MOD_RES
<222> LOCATION: (5)..(5)
<223> OTHER INFORMATION: Xaa(5) is type I, I', II, II', III or III'
      turn sequence
<220> FEATURE:
<221> NAME/KEY: MOD_RES
<222> LOCATION: (6)..(6)
<223> OTHER INFORMATION: Xaa(6) is Trp or Phe
<220> FEATURE:
<221> NAME/KEY: MOD_RES
<222> LOCATION: (7)..(7)
<223> OTHER INFORMATION: Xaa(7) is Thr, His, Val, Ile, Phe, or Tyr
<220> FEATURE:
<221> NAME/KEY: MOD_RES
<222> LOCATION: (8)..(8)
<223> OTHER INFORMATION: Xaa(8) is Trp or Val
<220> FEATURE:
<221> NAME/KEY: MOD_RES
<222> LOCATION: (9)..(9)
<223> OTHER INFORMATION: Xaa(9) is Lys or Thr
<220> FEATURE:
<221> NAME/KEY: MOD_RES
<222> LOCATION: (10)..(10)
<223> OTHER INFORMATION: Xaa(10) is absent or is Glu when Xaa(9) is Thr
<220> FEATURE:
<221> NAME/KEY: misc_feature
<222> LOCATION: (11)..(11)
<223> OTHER INFORMATION: Xaa(11) can be any naturally occurring amino
      acid

<400> SEQUENCE: 48

Xaa Xaa Trp Xaa Xaa Xaa Xaa Xaa Xaa Xaa Xaa
1               5                   10

<210> SEQ ID NO 49
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(4)
<223> OTHER INFORMATION: type I' turn sequence

<400> SEQUENCE: 49

Glu Asn Gly Lys
1

<210> SEQ ID NO 50
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(4)
<223> OTHER INFORMATION: type II' turn sequence

<400> SEQUENCE: 50

Glu Gly Asn Lys
1

<210> SEQ ID NO 51
<211> LENGTH: 11
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MISC_FEATURE
<222> LOCATION: (1)..(11)
<223> OTHER INFORMATION: GB1 peptide represented by Formula II
<220> FEATURE:
<221> NAME/KEY: MOD_RES
<222> LOCATION: (1)..(1)
<223> OTHER INFORMATION: Xaa(1) is Arg, Gly, or Lys
<220> FEATURE:
<221> NAME/KEY: MOD_RES
<222> LOCATION: (2)..(2)
<223> OTHER INFORMATION: Xaa(2) is absent or is Glu when Xaa(1) is Gly
      or is Lys when Xaa(1) is Lys
<220> FEATURE:
<221> NAME/KEY: MOD_RES
<222> LOCATION: (4)..(4)
<223> OTHER INFORMATION: Xaa(4) is Gln or Thr
<220> FEATURE:
<221> NAME/KEY: MOD_RES
<222> LOCATION: (6)..(6)
<223> OTHER INFORMATION: Xaa(6) is type I, I', II,II', III or III' turn
      sequence
<220> FEATURE:
<221> NAME/KEY: MOD_RES
<222> LOCATION: (10)..(10)
<223> OTHER INFORMATION: Xaa(10) is Thr or Gln
<220> FEATURE:
<221> NAME/KEY: MOD_RES
<222> LOCATION: (11)..(11)
<223> OTHER INFORMATION: Xaa(11) is absent or Glu when Xaa(10) is Gln,
      or is Glu when Xaa(10) is Thr

<400> SEQUENCE: 51

Xaa Xaa Trp Xaa Tyr Xaa Phe Thr Val Xaa Xaa
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(11)
<223> OTHER INFORMATION: GB1 peptide represented by Formula II'
<220> FEATURE:
<221> NAME/KEY: MOD_RES
<222> LOCATION: (1)..(1)
<223> OTHER INFORMATION: Xaa(1) is Arg, Gly or Lys
<220> FEATURE:
<221> NAME/KEY: MOD_RES
<222> LOCATION: (2)..(2)
<223> OTHER INFORMATION: Xaa(2) is absent or Glu when Xaa(1) is Gly or
      Lys when Xaa(1) is Lys
<220> FEATURE:
<221> NAME/KEY: MOD_RES
<222> LOCATION: (6)..(6)
<223> OTHER INFORMATION: Xaa(6) is type I, I', II, II', III or III' turn
      sequence
<220> FEATURE:
<221> NAME/KEY: MOD_RES
<222> LOCATION: (10)..(10)
<223> OTHER INFORMATION: Xaa(10) is Thr or Gln

<400> SEQUENCE: 52

Xaa Xaa Trp Thr Tyr Xaa Phe Thr Val Xaa Glu
1               5                   10

<210> SEQ ID NO 53
<211> LENGTH: 11
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MISC_FEATURE
<222> LOCATION: (1)..(11)
<223> OTHER INFORMATION: HP peptide represented by Formula III
<220> FEATURE:
<221> NAME/KEY: MOD_RES
<222> LOCATION: (2)..(2)
<223> OTHER INFORMATION: Xaa(2) is absent or Lys
<220> FEATURE:
<221> NAME/KEY: MOD_RES
<222> LOCATION: (3)..(3)
<223> OTHER INFORMATION: Xaa(3) is Trp or Tyr
<220> FEATURE:
<221> NAME/KEY: MOD_RES
<222> LOCATION: (4)..(4)
<223> OTHER INFORMATION: Xaa(4) is Val or Thr
<220> FEATURE:
<221> NAME/KEY: MOD_RES
<222> LOCATION: (6)..(6)
<223> OTHER INFORMATION: Xaa(6) is type I, I', II, II', III or III' turn
       sequence
<220> FEATURE:
<221> NAME/KEY: MOD_RES
<222> LOCATION: (7)..(7)
<223> OTHER INFORMATION: Xaa(7) is Trp or Ala
<220> FEATURE:
<221> NAME/KEY: MOD_RES
<222> LOCATION: (9)..(9)
<223> OTHER INFORMATION: Xaa(9) is Trp or Val
<220> FEATURE:
<221> NAME/KEY: MOD_RES
<222> LOCATION: (10)..(10)
<223> OTHER INFORMATION: Xaa(10) is Glu or Gln
<220> FEATURE:
<221> NAME/KEY: MOD_RES
<222> LOCATION: (11)..(11)
<223> OTHER INFORMATION: Xaa(11) is absent or Glu when Xaa(10) is Gln

<400> SEQUENCE: 53

Lys Xaa Xaa Xaa Trp Xaa Xaa Thr Xaa Xaa Xaa
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: beta-hairpin peptide represented by Formula IV
<220> FEATURE:
<221> NAME/KEY: MOD_RES
<222> LOCATION: (1)..(1)
<223> OTHER INFORMATION: Xaa(1) is Lys or Gly
<220> FEATURE:
<221> NAME/KEY: MOD_RES
<222> LOCATION: (2)..(2)
<223> OTHER INFORMATION: Xaa(2) is absent or is Thr when Xaa(1) is Lys
<220> FEATURE:
<221> NAME/KEY: MOD_RES
<222> LOCATION: (3)..(3)
<223> OTHER INFORMATION: Xaa(3) is Trp or Tyr
<220> FEATURE:
<221> NAME/KEY: MOD_RES
<222> LOCATION: (4)..(4)
<223> OTHER INFORMATION: Xaa(4) is type I, type I',type II, type II',
     type III or type III' turn sequence
<220> FEATURE:
<221> NAME/KEY: MOD_RES
<222> LOCATION: (6)..(6)
<223> OTHER INFORMATION: Xaa(6) is Thr or Gly
<220> FEATURE:
<221> NAME/KEY: MOD_RES
<222> LOCATION: (7)..(7)
```

-continued

<223> OTHER INFORMATION: Xaa(7) is absent or is Glu when Xaa(6) is Thr

<400> SEQUENCE: 54

Xaa Xaa Xaa Xaa Trp Xaa Xaa
1               5

<210> SEQ ID NO 55
<211> LENGTH: 66
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(66)
<223> OTHER INFORMATION: BPB-F1
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t

<400> SEQUENCE: 55
ttctatgcgg cccagctggc cnnknnknnk nnknnknnkg gatcttggac atgggaaaac    60
ggaaaa                                                              66

<210> SEQ ID NO 56
<211> LENGTH: 69
<212> TYPE: DNA
<213> ORGANISM: Artificial Sequence
<220> FEATURE:
<223> OTHER INFORMATION: Sythnetic Construct
<220> FEATURE:
<221> NAME/KEY: misc_feature
<222> LOCATION: (1)..(69)
<223> OTHER INFORMATION: BPB-F2
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)

```
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t

<400> SEQUENCE: 56
aacagtttct gcggccgctc ctcctccmnn mnnmnnmnnm nnmnntccct tccatgtcca      60
ttttccgtt                                                              69

<210> SEQ ID NO 57
<211> LENGTH: 28
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(28)
<223> OTHER INFORMATION: EDB_F1 primer

<400> SEQUENCE: 57
ttcataacat atgccagagg tgccccaa                                         28

<210> SEQ ID NO 58
<211> LENGTH: 106
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(106)
<223> OTHER INFORMATION: EDB_B1 primer

<400> SEQUENCE: 58
attggatcct tacgtttgtt gtgtcagtgt agtaggggca ctctcgccgc cattaatgag      60
agtgataacg ctgatatcat agtcaatgcc cggctccagc cctgtg                    106

<210> SEQ ID NO 59
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(24)
<223> OTHER INFORMATION: VEGF_F1 primer

<400> SEQUENCE: 59
atagaattcg cacccatggc agaa                                             24

<210> SEQ ID NO 60
<211> LENGTH: 45
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(45)
<223> OTHER INFORMATION: VEGF_B1 primer

<400> SEQUENCE: 60
attaagcttt caccgcctcg gcttgtcaca attttcttgt cttgc                      45
```

```
<210> SEQ ID NO 61
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(32)
<223> OTHER INFORMATION: a peptide fragment of nAchR

<400> SEQUENCE: 61

Ser Gly Glu Trp Val Ile Lys Glu Ala Arg Gly Trp Lys His Trp Val
1               5                   10                  15

Phe Tyr Ser Cys Cys Pro Thr Thr Pro Tyr Leu Asp Ile Thr Tyr His
            20                  25                  30

<210> SEQ ID NO 62
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(21)
<223> OTHER INFORMATION: phagemid sequence

<400> SEQUENCE: 62
gattacgcca agctttggag c                                           21

<210> SEQ ID NO 63
<211> LENGTH: 30
<212> TYPE: PRT
<213> ORGANISM: Artificial Sequence
<220> FEATURE:
<223> OTHER INFORMATION: Synthetic Construct

<400> SEQUENCE: 63

His Cys Ser Ser Ala Val Gly Lys Lys Trp Thr Tyr Asn Pro Ala Thr
1               5                   10                  15

Gly Lys Phe Thr Val Gln Glu Gly Ile Ile Arg Leu Glu Gln
            20                  25                  30

<210> SEQ ID NO 64
<211> LENGTH: 26
<212> TYPE: PRT
<213> ORGANISM: Artificial Sequence
<220> FEATURE:
<223> OTHER INFORMATION: Synthetic Construct

<400> SEQUENCE: 64

His Cys Ser Ser Ala Val Gly Lys Thr Trp Asn Pro Ala Thr Gly Lys
1               5                   10                  15

Trp Thr Glu Gly Ile Ile Arg Leu Glu Gln
            20                  25
```